United States Patent
Xie et al.

(10) Patent No.: US 9,072,751 B2
(45) Date of Patent: *Jul. 7, 2015

(54) NA/K-ATPASE LIGAND

(71) Applicant: The University of Toledo, Toledo, OH (US)

(72) Inventors: Zi-Jian Xie, Saline, MI (US); Joseph I. Shapiro, Toledo, OH (US)

(73) Assignee: The University of Toledo, Toledo, OH (US)

( * ) Notice: Subject to any disclaimer, the term of this patent is extended or adjusted under 35 U.S.C. 154(b) by 135 days.

This patent is subject to a terminal disclaimer.

(21) Appl. No.: 13/850,218

(22) Filed: Mar. 25, 2013

(65) Prior Publication Data
US 2014/0128356 A1    May 8, 2014

Related U.S. Application Data

(62) Division of application No. 12/087,976, filed as application No. PCT/US2007/002365 on Jan. 30, 2007.

(60) Provisional application No. 60/763,783, filed on Jan. 31, 2006.

(51) Int. Cl.
| | |
|---|---|
| A61K 31/585 | (2006.01) |
| A61K 31/7048 | (2006.01) |
| A61K 31/56 | (2006.01) |
| A61K 31/58 | (2006.01) |
| A61K 8/63 | (2006.01) |
| A61Q 19/08 | (2006.01) |

(52) U.S. Cl.
CPC .............. *A61K 31/585* (2013.01); *A61K 31/58* (2013.01); *A61K 31/7048* (2013.01); *A61K 8/63* (2013.01); *A61K 31/56* (2013.01); *A61K 2800/782* (2013.01); *A61Q 19/08* (2013.01)

(58) Field of Classification Search
CPC ..... A61K 31/585; A61K 31/56; A61K 31/58; A61K 31/7048
See application file for complete search history.

(56) References Cited

U.S. PATENT DOCUMENTS

| | | | |
|---|---|---|---|
| 5,989,591 A | 11/1999 | Nagi | |
| 2002/0168425 A1* | 11/2002 | Nakayama et al. | 424/725 |
| 2005/0271606 A1* | 12/2005 | Iwasaki et al. | 424/59 |
| 2006/0135468 A1 | 6/2006 | Khodadoust | |
| 2006/0205679 A1* | 9/2006 | Streeper et al. | 514/26 |
| 2009/0226513 A1 | 9/2009 | Xie et al. | |

FOREIGN PATENT DOCUMENTS

| | | |
|---|---|---|
| WO | 2007089688 A2 | 8/2007 |
| WO | 2007130124 A1 | 11/2007 |

OTHER PUBLICATIONS

Yang et al. 2005, PNAS, vol. 102, No. 27, pp. 9361-9636.*
Canadian Notice of Allowance, Application No. 2641303, dated Jan. 7, 2013.
Chinese Office Action, Application No. 200780003862.8 dated May 30, 2012.
Chinese Office Action, Application No. 200780003862.8 dated Dec. 5, 2012.
Chong et al., "Endogenous and Synthetic Inhibitors of the SRC-Family Protein Tyrosine Kinases," Biochimica et Biophysica Acta., Dec. 2005, vol. 1754, Nos. 1-2, pp. 210-220.
EP Communication Pursuant to Article 94(3) EPC, Application No. 07762999.6, dated Oct. 13, 2009.
EP Communication Pursuant to Article 94(3) EPC, Application No. 07762999.6, dated Jul. 23, 2010.
EP Search Report, Application No. 09833816.3, dated Apr. 12, 2012.
Japanese Office Action, Application No. 2008-553283, dated Jun. 22, 2012.
Li et al., "Low Doses of Ouabain Protect from Serum Deprivation-Triggered Apoptosis and Stimulate Kidney Cell Proliferation via Activaiton of NF-kB," Journal of American Society of Nephrology, 2006, vol. 17, pp. 1848-1857.
PCT International Preliminary Report on Patentability, PCT/US2011/021130 filed Jan. 13, 2011, dated Jul. 26, 2012.
PCT International Preliminary Report on Patentability, PCT/US2011/021127 filed Jan. 13, 2011, dated Jul. 26, 2012.
PCT Written Opinion, Application No. PCT/US07/02365, dated Dec. 20, 2007.
Schulte, R. et al., "Inhibition of the Activity of SRC and ABL Tyrosine Protein Kinases by the Binding of the Wiskott-Aldrich Syndrome Protein," Biochemistry, Aug. 2003, vol. 42, No. 31, pp. 9424-9430.
Susa et al., "SRC Inhibitors: Drugs for the Treatment of Osteoporosis, Cancer or Both?" Trends in Pharmacological Sciences, Dec. 2000, vol. 21, No. 12, pp. 489-495.
Yeatman, T.J., "A Renaissance for SRC," Nature Reviews Cancer, Jun. 2004, vol. 4, No. 6, pp. 470-480.

* cited by examiner

*Primary Examiner* — Kara R McMillian
(74) *Attorney, Agent, or Firm* — MacMillan, Sobanski & Todd, LLC

(57) ABSTRACT

Methods and compositions for detecting, treating, characterizing, and diagnosing interstitial lung and/or fibrotic diseases are described.

7 Claims, 21 Drawing Sheets

NA/K-ATPASE LIGAND

CROSS-REFERENCE TO RELATED APPLICATIONS

This application is a continuation application of Ser. No. 12/087,976 filed Jul. 31, 2008, now U.S. Pat. No. 8,906,891 issued Dec. 9, 2014, which claims the benefit of PCT/US2007/002365 filed Jan. 30, 2007, which claims priority to U.S. provisional patent application Ser. No. 60/763,783 filed Jan. 31, 2006, the entire disclosures of which are expressly incorporated herein by reference.

FIELD OF THE INVENTION

This invention relates to a pharmaceutical composition of an Na/K-ATPase ligand which will stimulate Na/K-ATPase signaling in a pharmaceutically or cosmetically acceptable vehicle. In one embodiment, the composition may be used to prevent the development of and treat a skin disorder. In another embodiment, the composition may be used to inhibit tissue fibrosis. We also have found this invention useful for the treatment of hypertension and wound closure.

BACKGROUND OF THE INVENTION

Compounds can be used as agents through topical or systemic application. A preparation for this purpose can include a carrier, a protectant, an antioxidant (such as vitamin C or E), and other pharmaceutical and pharmacological agents. It is also expected that such compounds can be used in a delivery system (oral, local application, injection or implantation) involving molecular recognition through which the compounds are delivered to target site. Such a delivery system may involve, among other methods, liposome techniques or immunological devices. Natural or synthetic chemicals that can modulate the production or cellular action of receptors and macromolecules are useful in the treatment of abnormalities such as skin diseases.

Over the past decades numerous investigators have devoted significant effort to the study of extracts of mammalian tissue and fluids in order to identify and confirm the existence of factors that may be involved in the regulation of $Na^+$, $K^+$-ATPase enzyme system. At present, considerable evidence has been produced supporting the existence of such an endogenous factor or family of factors that is believed to inhibit the $Na^+$, $K^+$-ATPase enzyme system. Moreover, these inhibitory properties implicate the involvement of such factors in several physiological roles. However, in spite of the extensive data produced by these early investigators, considerable controversy exists with respect to their mechanisms of action, thus the physiological significance of such factors.

BRIEF SUMMARY OF THE INVENTION

The present invention relates generally to the utilization of certain compounds for the control of certain disorders. We use a pharmaceutical composition, comprising: a pharmaceutically effective amount of at least one Na/K-ATPase ligand which will stimulate Na/K-ATPase signaling in a pharmaceutically acceptable vehicle.

The composition induces the interaction of the signaling Na/K-ATPase with lipids, protein kinases, phosphatases, ion channels, transporters, and other soluble and membrane proteins to form various signaling complexes termed Na/K-ATPase signalosomes. The process maintains normal skin structure and function. Thus, administration of an effective dose the invented pharmaceutical composition to the subject prevents the development of and treats a skin disorder in a subject in need of such prevention and treatment. The process includes the step of enhancing skin fibroblast collagen production by topical or injected administration of the pharmaceutical composition to prevent or reverse aging related loss of skin tone. The process also may include the steps of using the pharmaceutical composition as a topical or systemic enhancement to wound closure.

We have demonstrated that the Na/K-ATPase interacts with different lipids and proteins. These interactions result in the formation of multiple functional complexes that constitute the Na/K-ATPase signalosome. The realization that the Na/K-ATPase can regulate many important cellular functions and transmit the signal of CTS independent of its pumping function has promoted us to define molecular compositions of the Na/K-ATPase signalosome and the molecular mechanisms by which this signalosome functions. These studies have provided us with several new targets for molecular interventions of the cellular function, thus novel therapeutics and diagnostics. In one embodiment, we present one of those applications to prevent or reverse aging related loss of skin tone as well as to accelerate wound healing.

We discovered a relationship between high circulating levels of the cardiotonic steroid, marinobufagenin (MBG), and cardiac fibrosis in experimental renal failure induced by partial nephrectomy (PNx). In short, we observed that PNx animals had substantial cardiac fibrosis. This fibrosis could also be induced by administration of MBG to achieve similar blood levels. The fibrosis could be attenuated by immunizing animals against MBG prior to PNx surgery. Representative immunohistochemistry images are shown below for illustration.

Other objects and advantages of the present invention will become apparent to those skilled in the art upon a review of the following detailed description of the preferred embodiments and the accompanying drawings.

DETAILED DESCRIPTION OF THE INVENTION

In one embodiment, the composition induces the formation of various signaling complexes termed Na/K-ATPase signalosomes. n another embodiment, the pharmaceutical composition is a pharmacologically effective amount of at least one inhibitor of Na/K-ATPase signaling in a pharmaceutically acceptable vehicle. The composition functions as an inhibitor of signal transduction through the Na/K-ATPase. Preferably, the treating of a skin disorder in a subject in need of such treatment comprises the step of administrating to the subject of an effective therapeutic amount of the pharmaceutical composition.

More specifically, the treatment includes the step of using the pharmaceutical composition as a topical or injected tool to reverse or prevent excessive dermal scar formation. In another embodiment, the treating is inhibiting cardiac fibrosis in a subject in need of such treatment comprising the step of administering to the subject an effective therapeutic amount of pharmaceutical composition. The pharmaceutical composition may be in a dosage form selected from the group consisting of tablet, pill, suspension tablet, powder, lozenge, sachet, cachet, elixir, suspension, emulsion, solution, syrup, aerosol, ointment, soft gelatin capsule, and hard gelatin capsule, suppository creams, lotions, solutions, gels and pastes.

The Na/K-ATPase ligands include but not limited to a group of chemicals generically called cardiotonic steroids (e.g., cardenolides and bufadienolides) that are derived from either plants or animals or semi-synthesized. The inhibitors include but not limited to those that disrupt the Na/K-ATPase interaction with its signaling partners such as EGF receptor, Src kinase and caveolin-1. The subjects in need of treatment would include (but not limited to) those with systemic fibrosing conditions such as Scleroderma as well as those with localized fibrosing conditions such as liver cirrhosis due to viral or alcoholic hepatitis, progressive cardiac failure associated with renal disease and/or atherosclerosis as well as progressive renal disease from glomerlonephritis, diabetes and hypertension.

The Na/K-ATPase belongs to the family of P-type ATPases that are essential for an organism to convert ATP into electric and chemical gradients across the membranes. The Na/K-ATPase expresses in almost all mammalian cells and pumps Na+ and K+ across cell membrane using the energy generated through hydrolysis of ATP. During the last few years, our laboratories have obtained evidence that the Na/K-ATPases also functions as an important cellular signal transducer. We now suggest that there are at least two separate pools of the Na/K-ATPase, one functions as an ion pump while the other engages in interaction with lipids, protein kinases, phosphatases, ion channels, transporters, and other soluble and membrane proteins to form various signaling complexes termed Na/K-ATPase signalosomes.

Figure 1:
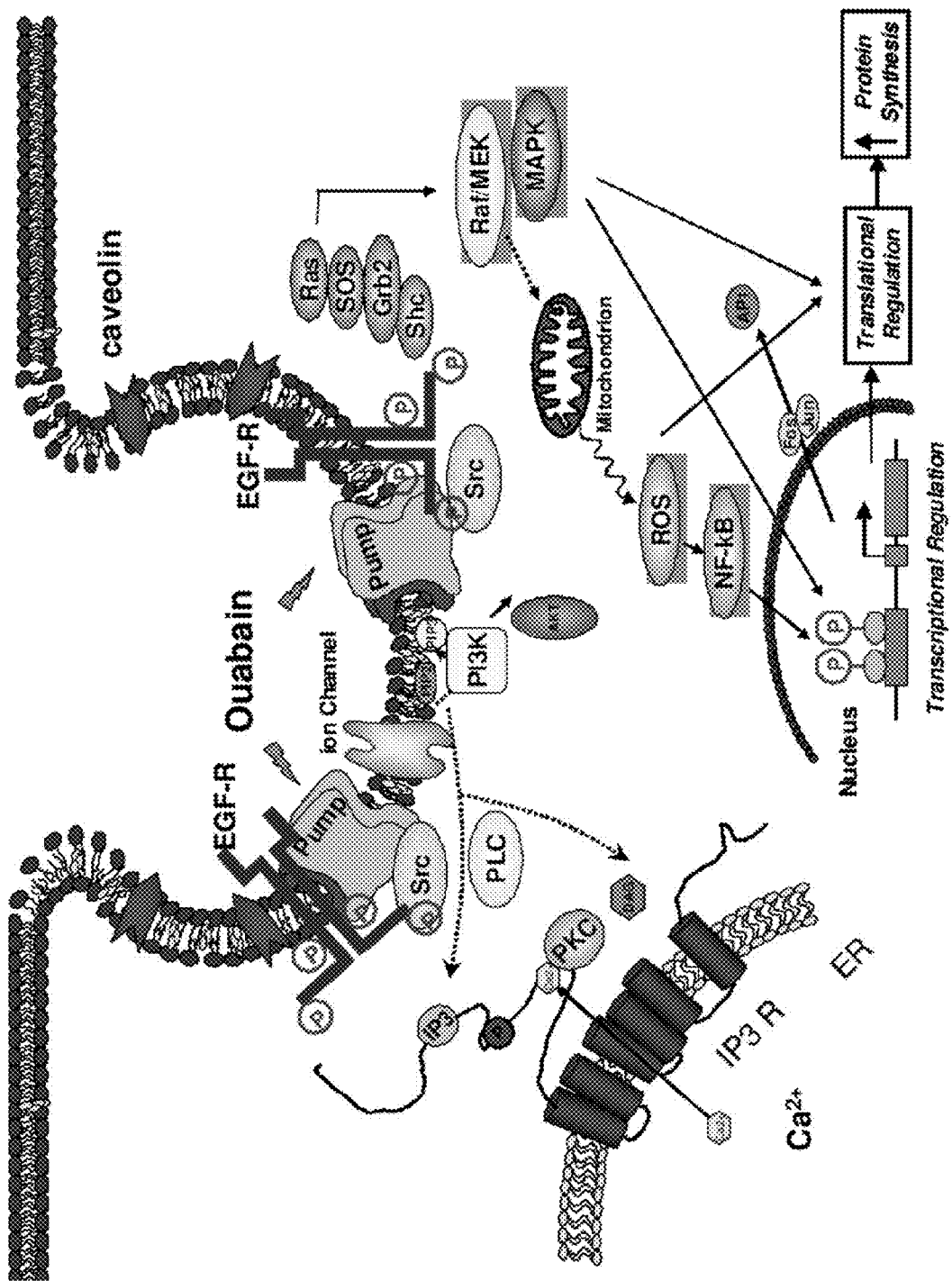
FIG. 1 shows the pathway of Na/K-ATPase signalosomes.

FIG. 1 is a schematic depicting sodium pump signaling in cardiac myocytes. In the presence of a cardiotonic steroid, Na/K-ATPase is converted to a signal transducer, which complexes with Src and the epidermal growth factor receptor. A signal cascade is initiated, which depends on Ras and results in the generation of reactive oxygen species (ROS) and activation of ERK. This, in turn, leads to altered gene expression, including decreases in SERCA expression, as well as alterations in calcium cycling.

Figure 2:
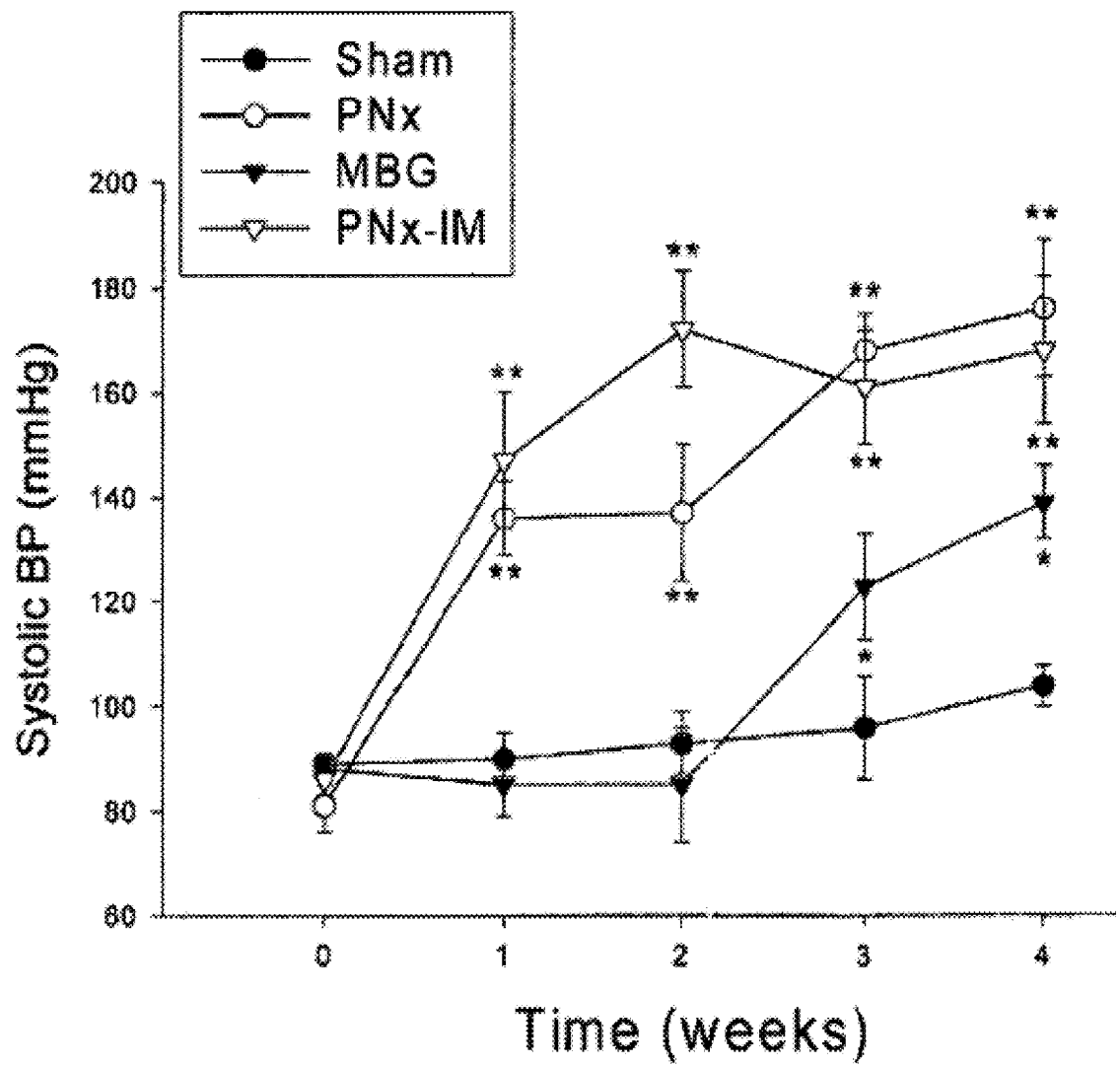
FIG. 2 shows the effect of marinobufagenin (MBG) on systolic BP.

FIG. 2 shows MBG produces functional and anatomic changes consistent with cardiac hypertrophy. (a) Systolic BP 4 weeks after sham operation (Sham, n=8), partial nephrectomy (PNx, n=B), MBG infusion (MBG, n=10), or immunization against MBG before partial nephrectomy (PNx-IM, n=8). (b) Representative mode echocardiograms in the 4 groups of rats. (c) Posterior wall thickness. (d) left ventricular end diastolic diameter (e) left ventricular end systolic diameter, and (f) FS 4 weeks after Sham (n=8) PNx (n=10), MBG (n=9), or PNx-IM (n=16). *P<0.05 vs PNx; ##P<0.01 vs. PNx.

Figure 3:
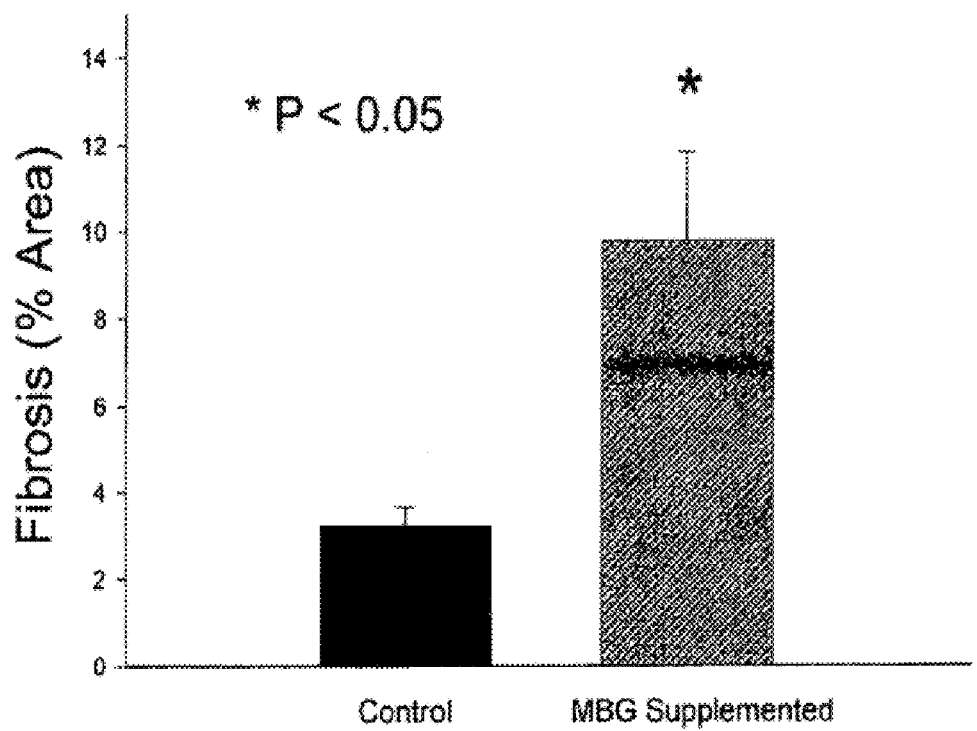
FIG. 3 shows the effect of MGB on renal fibrosis.

FIG. 3 shows the effect of MBG on renal fibrosis.

Figure 4:
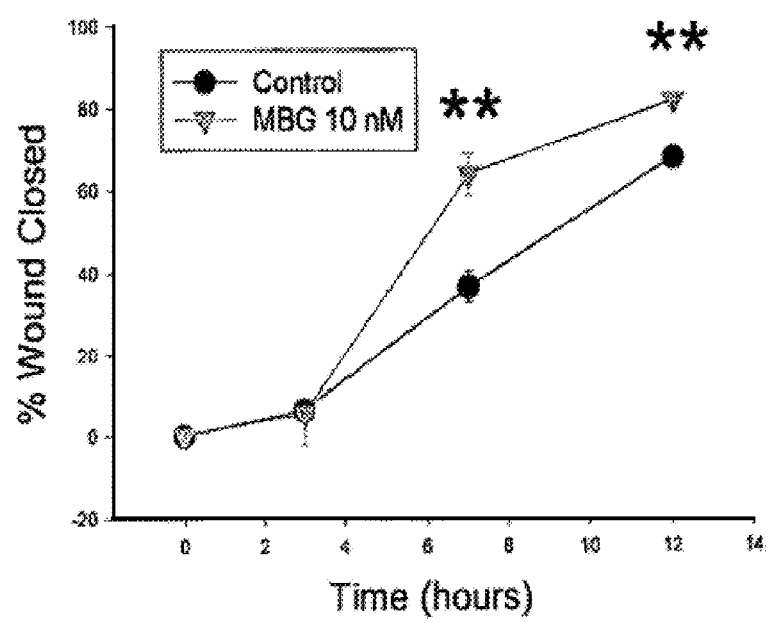
FIG. 4 shows the effect of MGB accelerates wound healing.

FIG. 4 shows the effect of MBG accelerates wound healing.

Figure 5A:
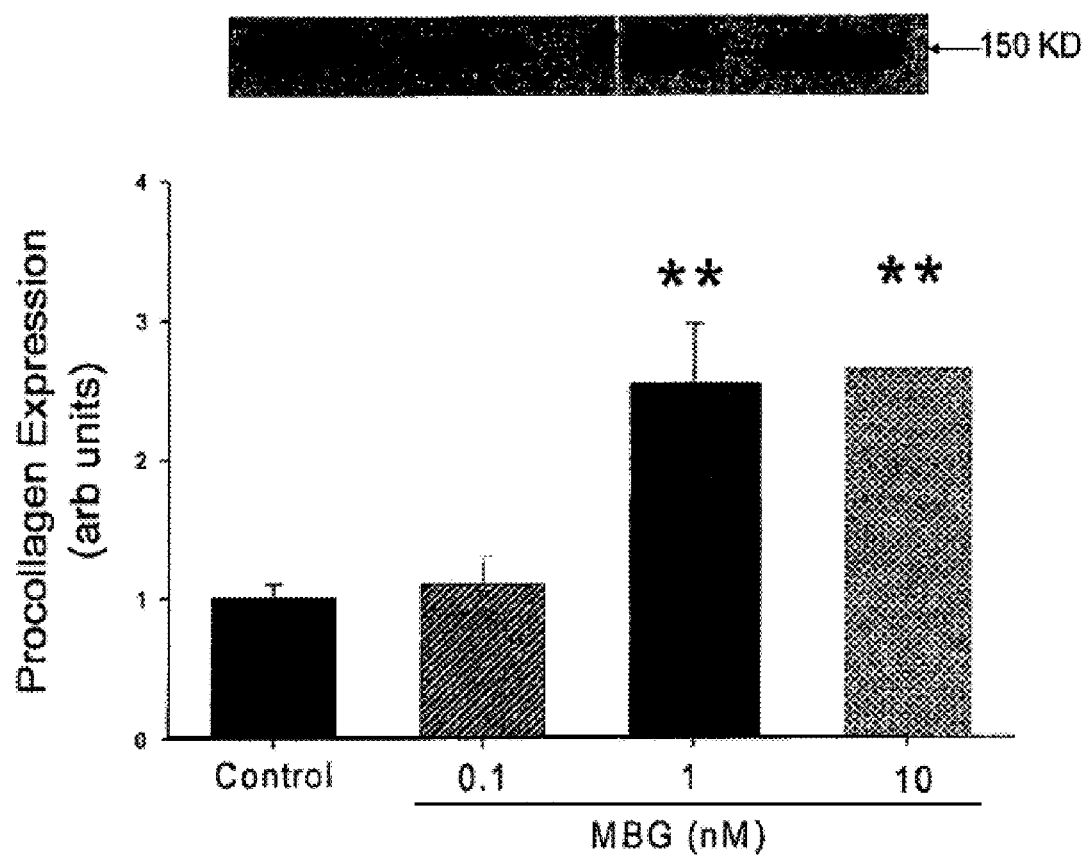
FIGS. 5(a) and 5(b) show the effect of MGB on procollagen expression.
Figure 5B:
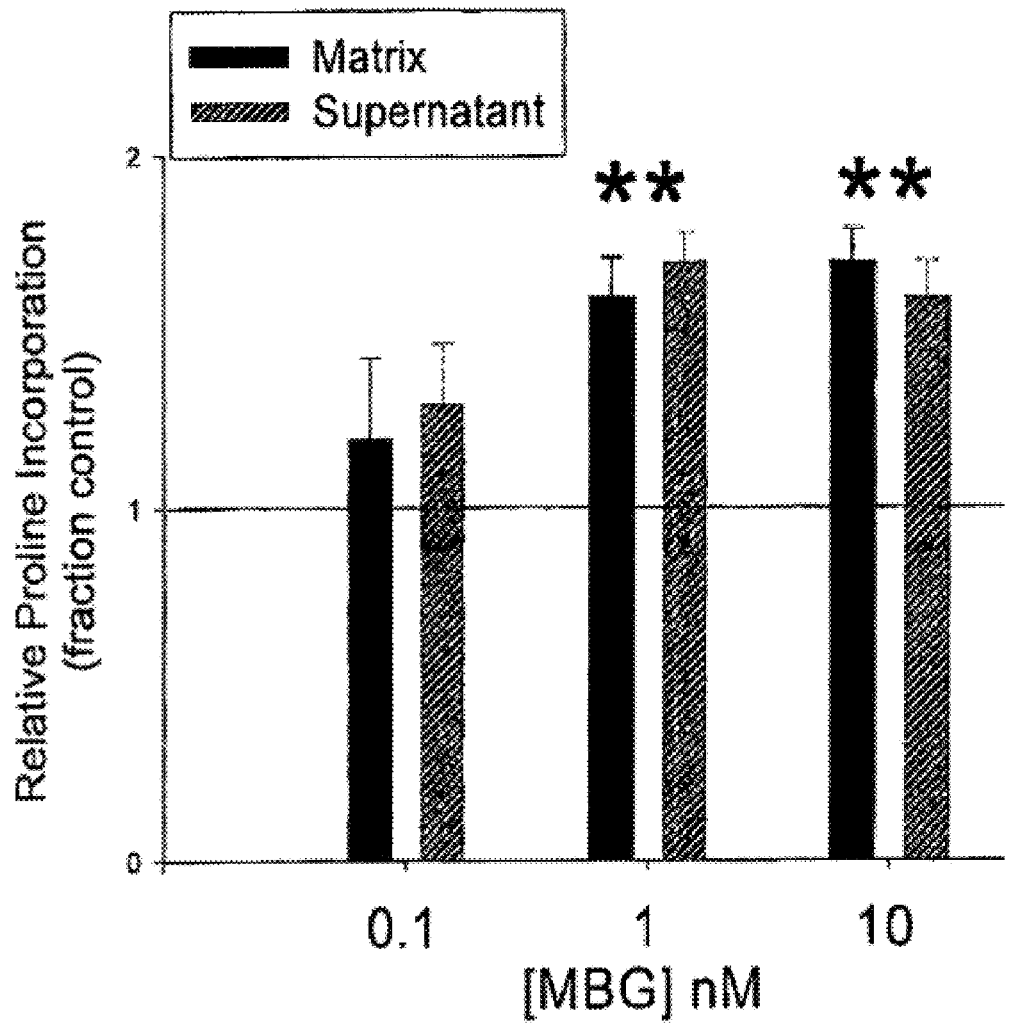
Figure 6A:
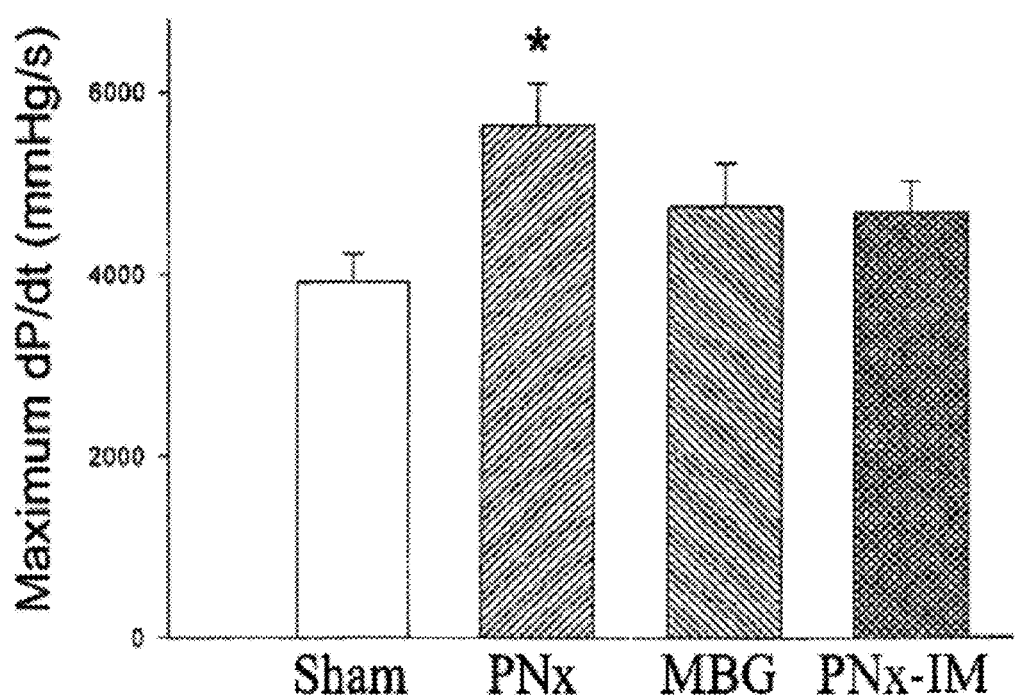
FIG. 6(a) shows dP/dt data.
Figure 6B:
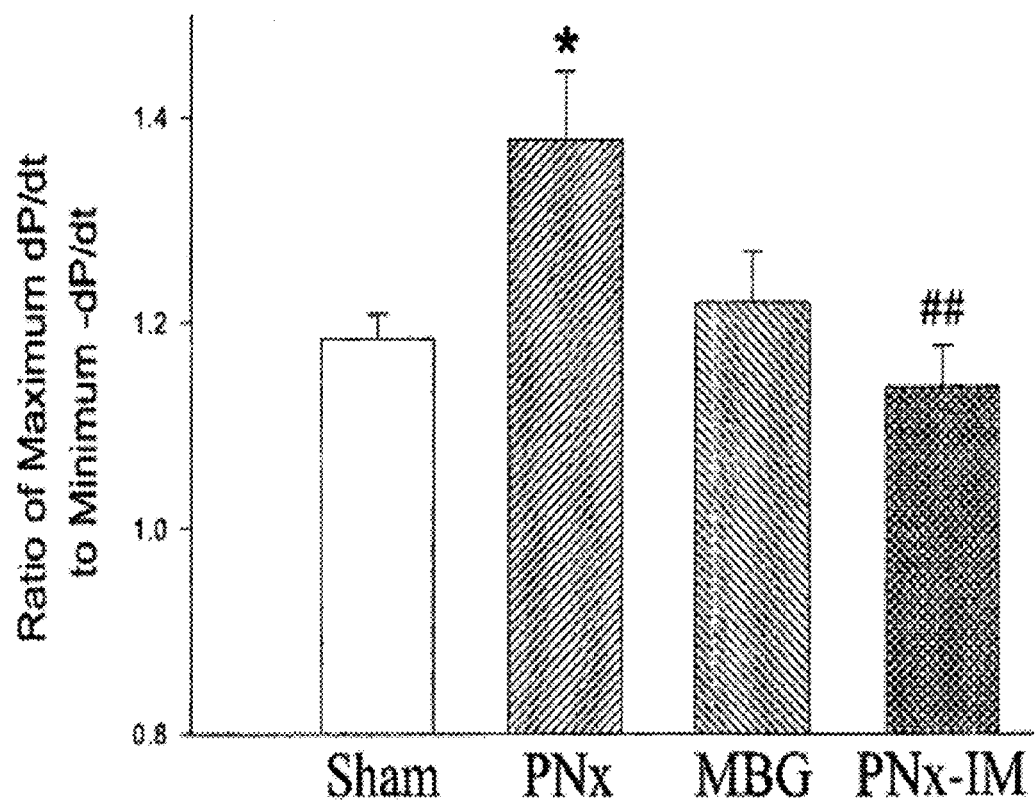
FIG. 6(b) shows dP/dt data.
Figure 6C:
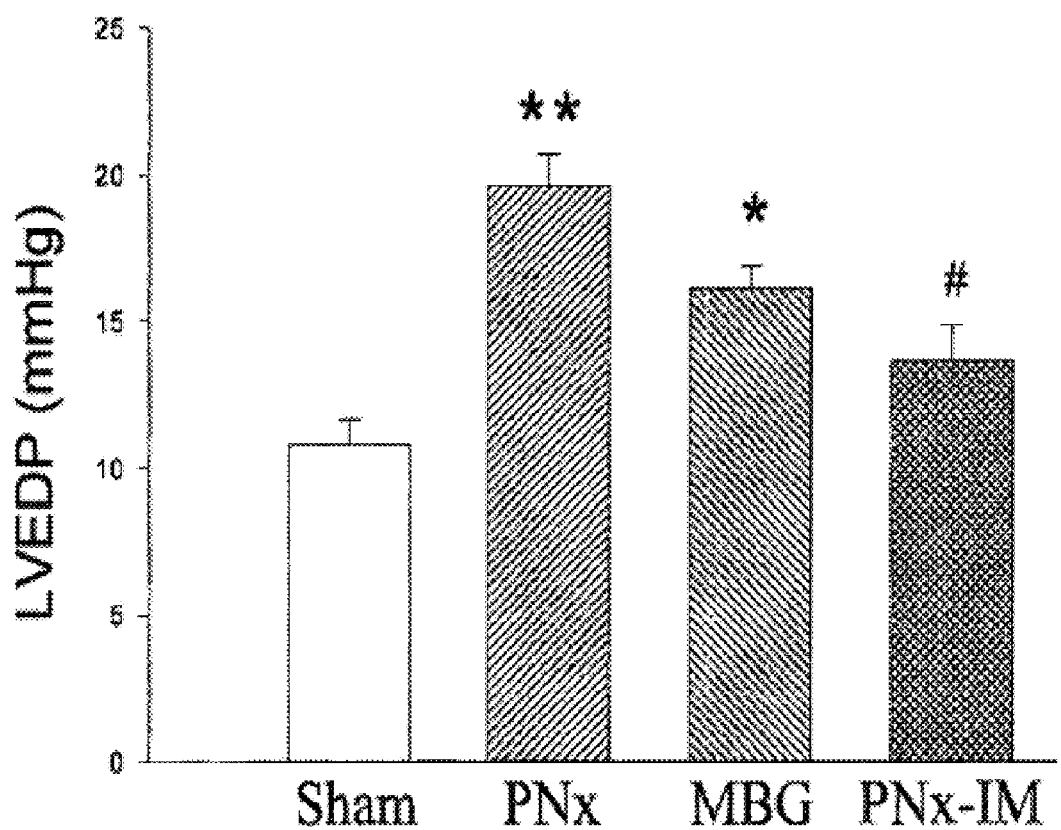
FIG. 6(c) shows LVEDP data.
Figure 6D:
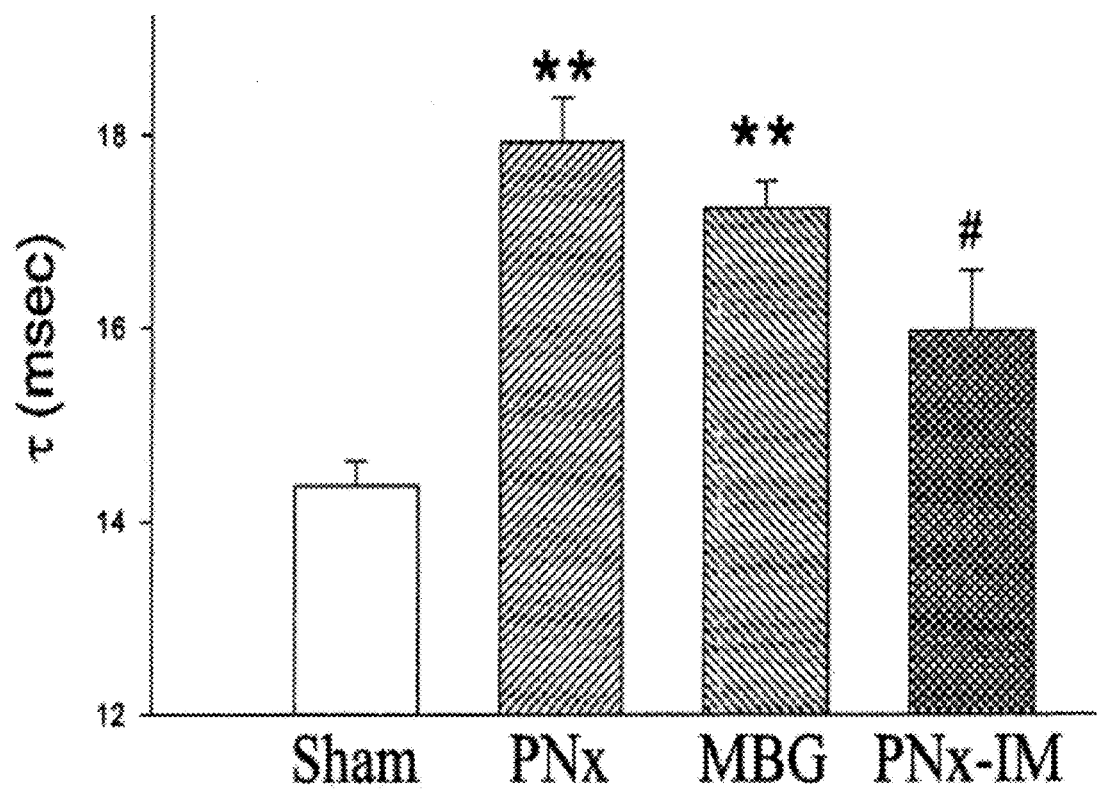
FIG. 6(d) shows MSEC data.
Figure 7A:
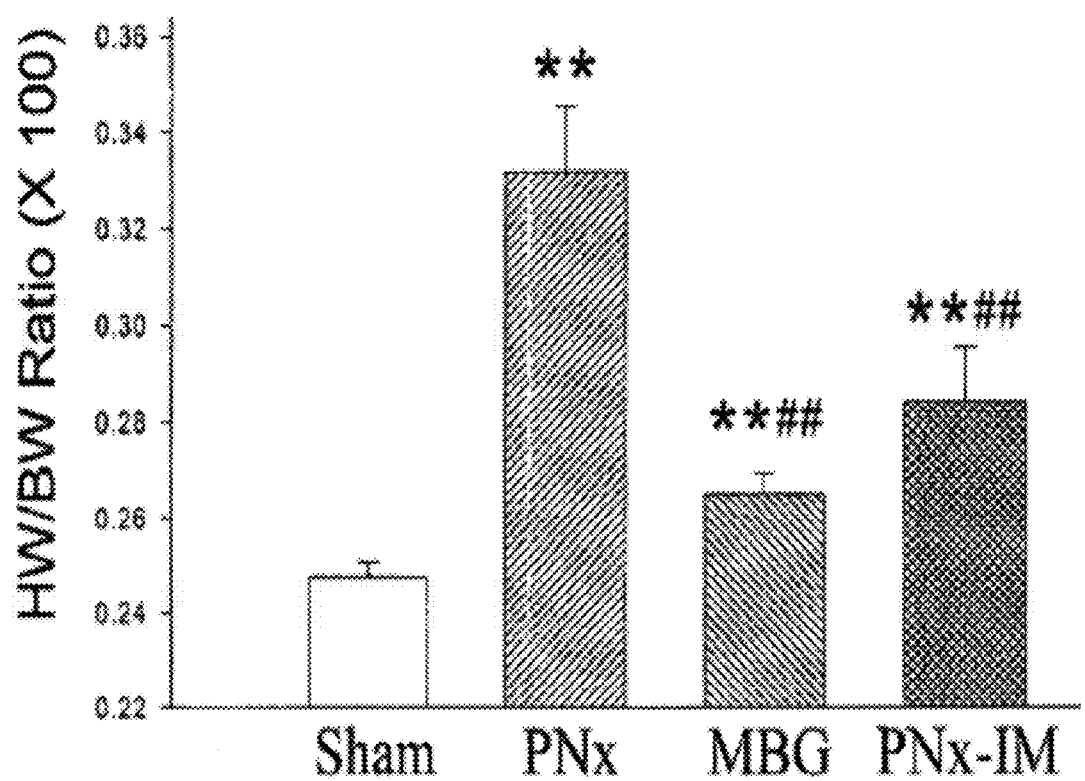
FIG. 7(a) shows HW/BW data.
Figure 7B:
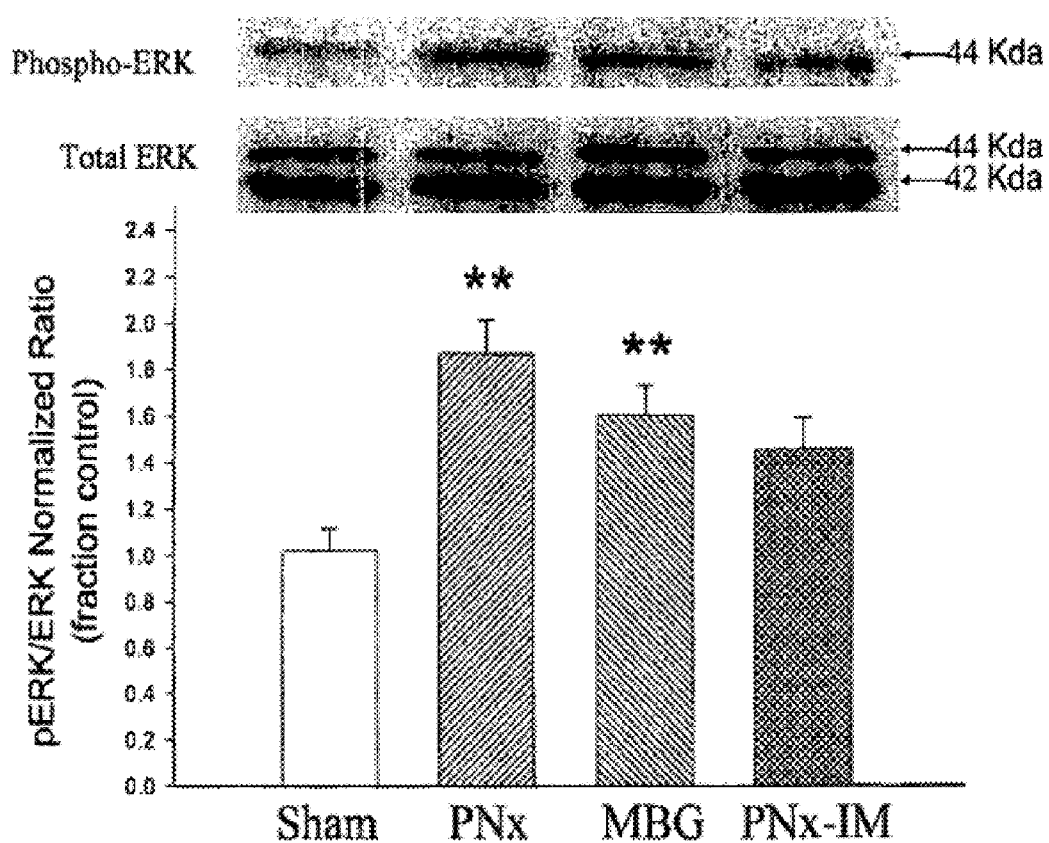
FIG. 7(b) shows procollagen expression demonstrated with Western blot.
Figure 7C:
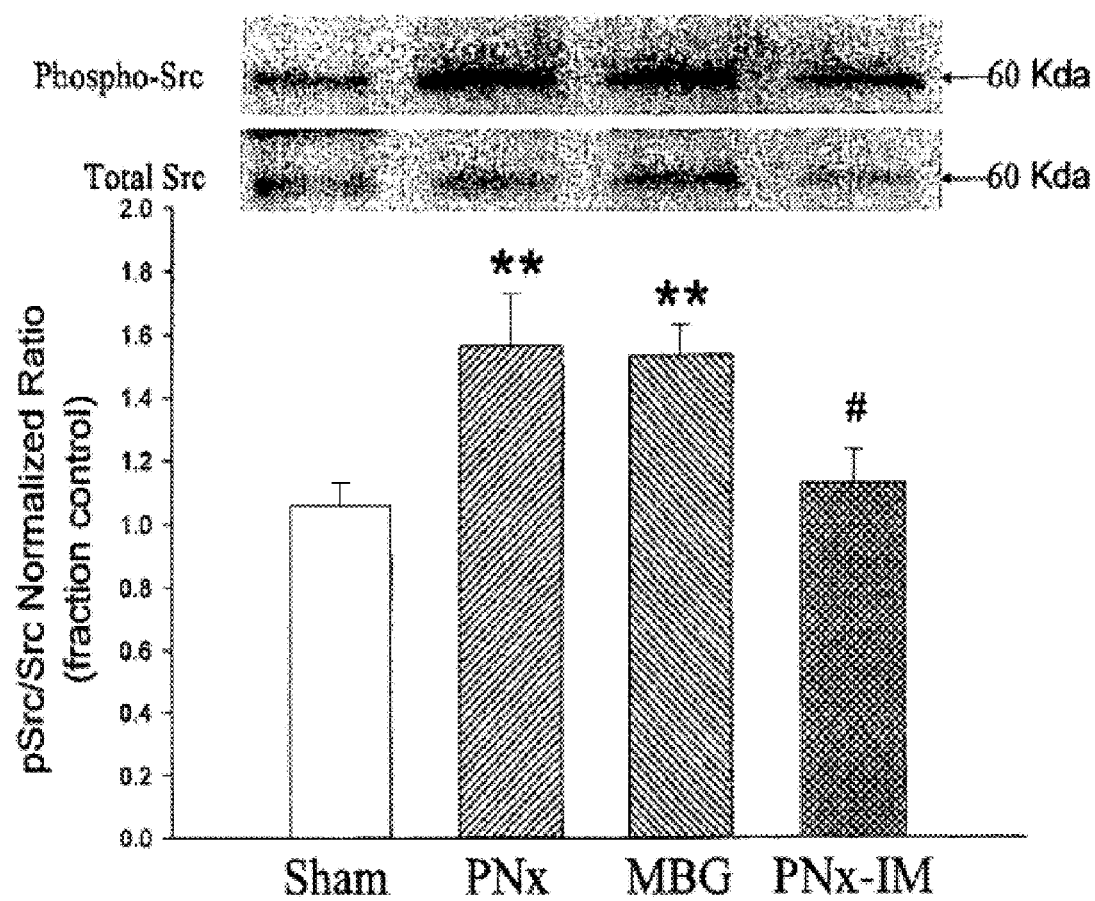
FIG. 7(c) shows procollagen expression demonstrated with Western blot.
Figure 7D:
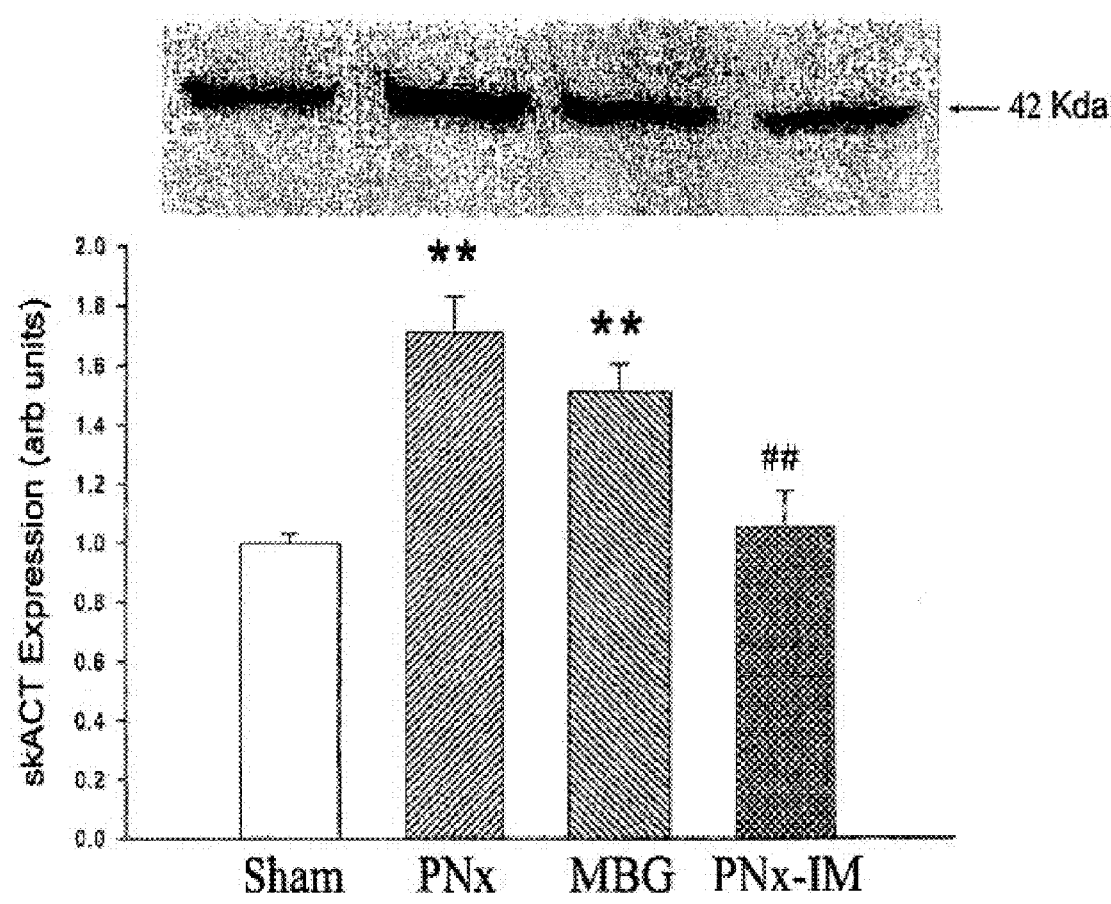
FIG. 7(d) shows procollagen expression demonstrated with Western blot.
Figure 7E:
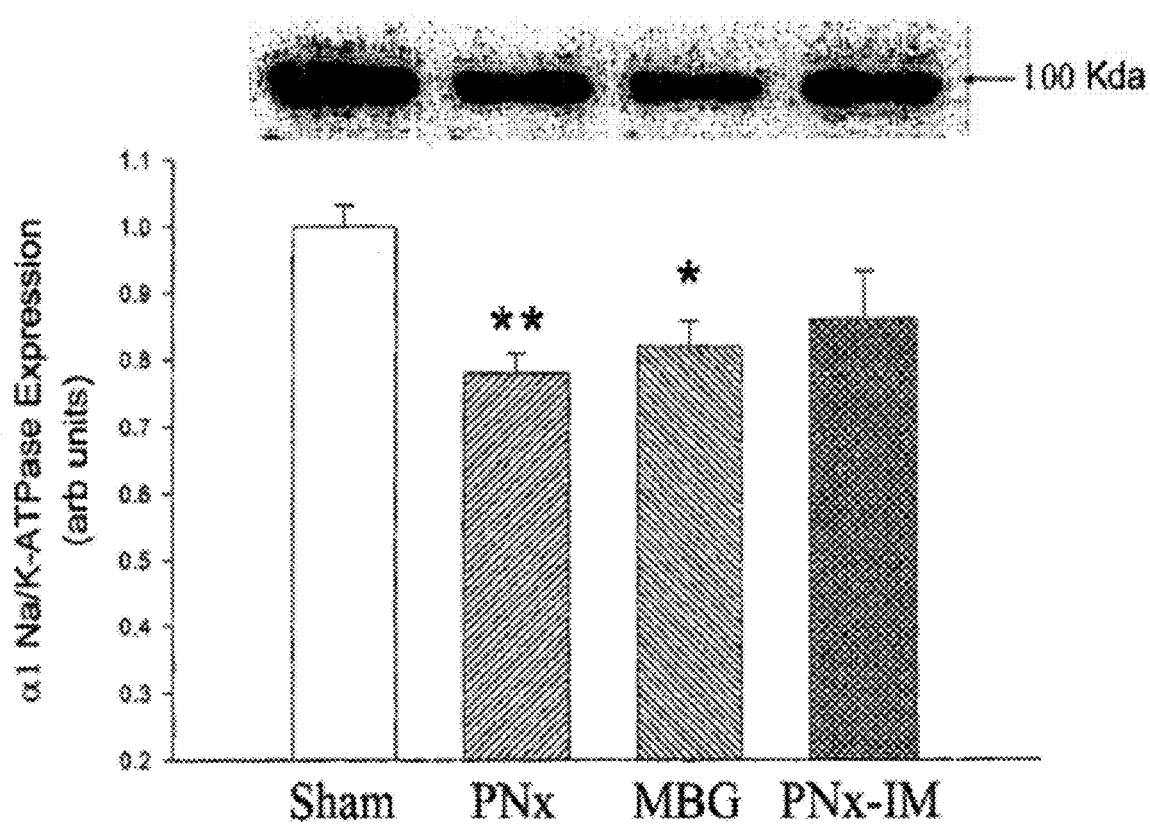
FIG. 7(e) shows procollagen expression demonstrated with Western blot.
Figure 7F:
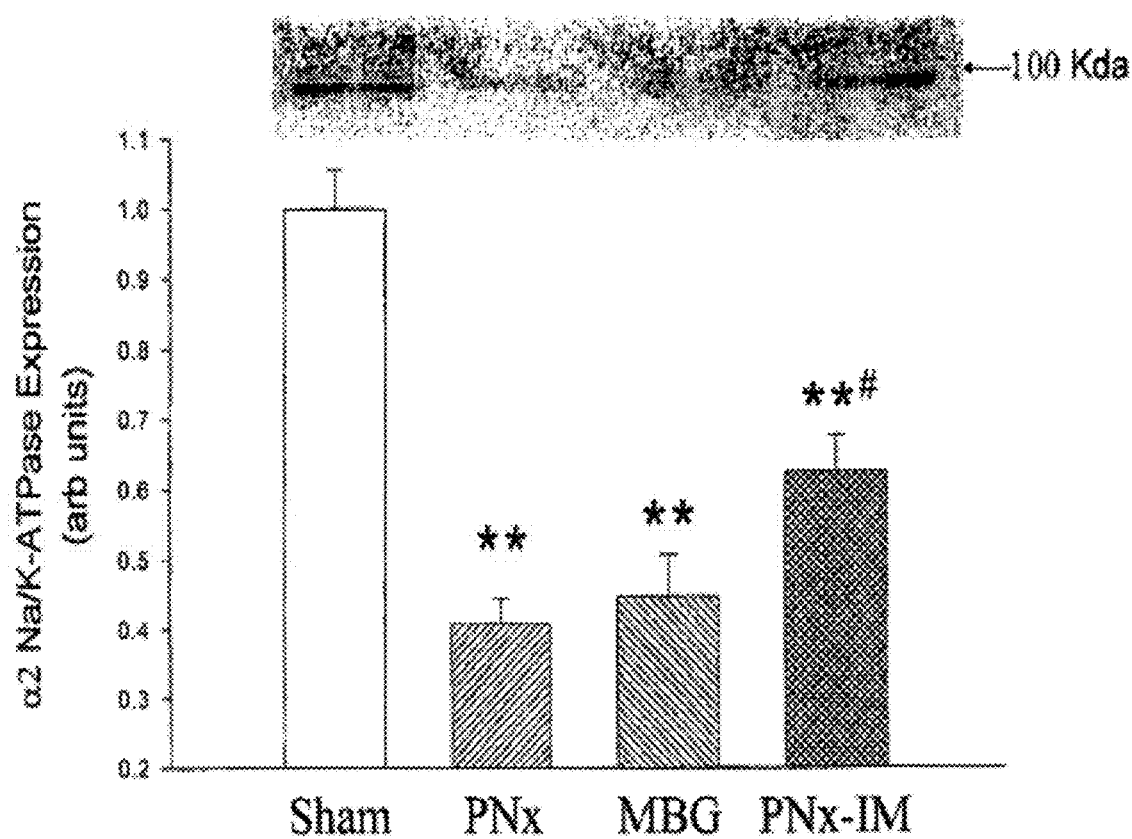
FIG. 7(f) shows Na/K-ATPase expression demonstrated with Western blot.
Figure 7G:
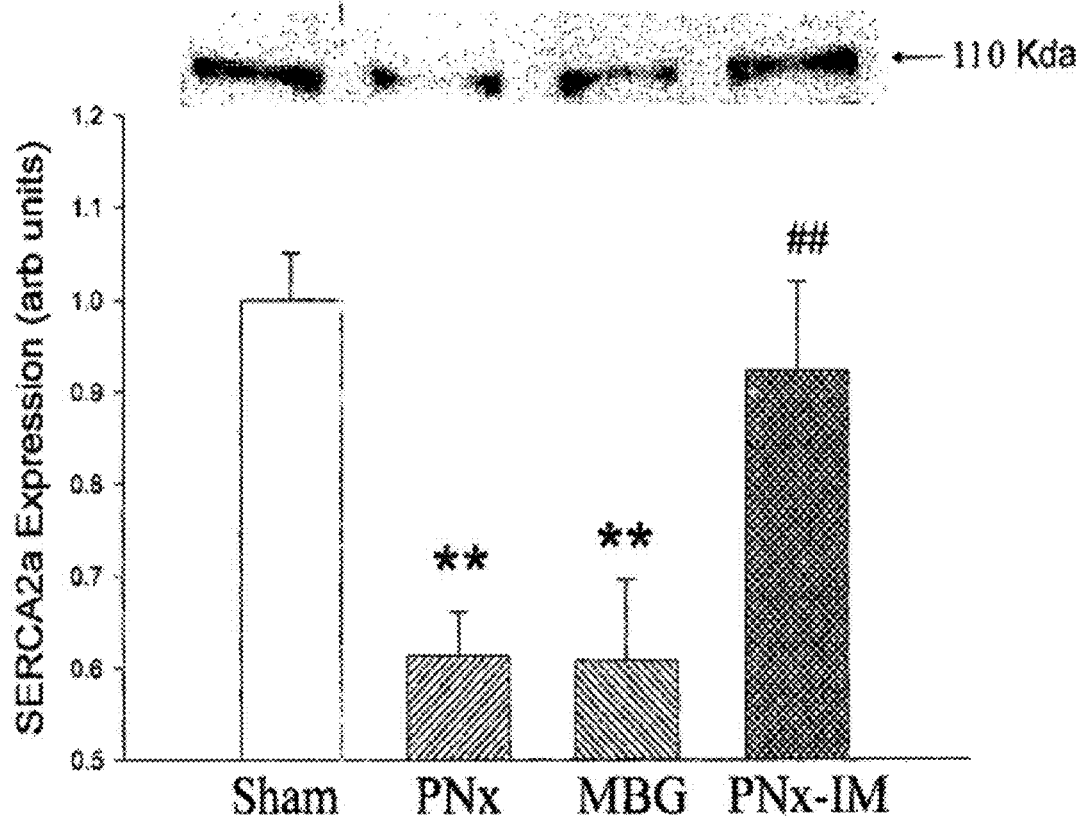
FIG. 7(g) shows SERCA expression demonstrated with Western blot.
Figure 7H:
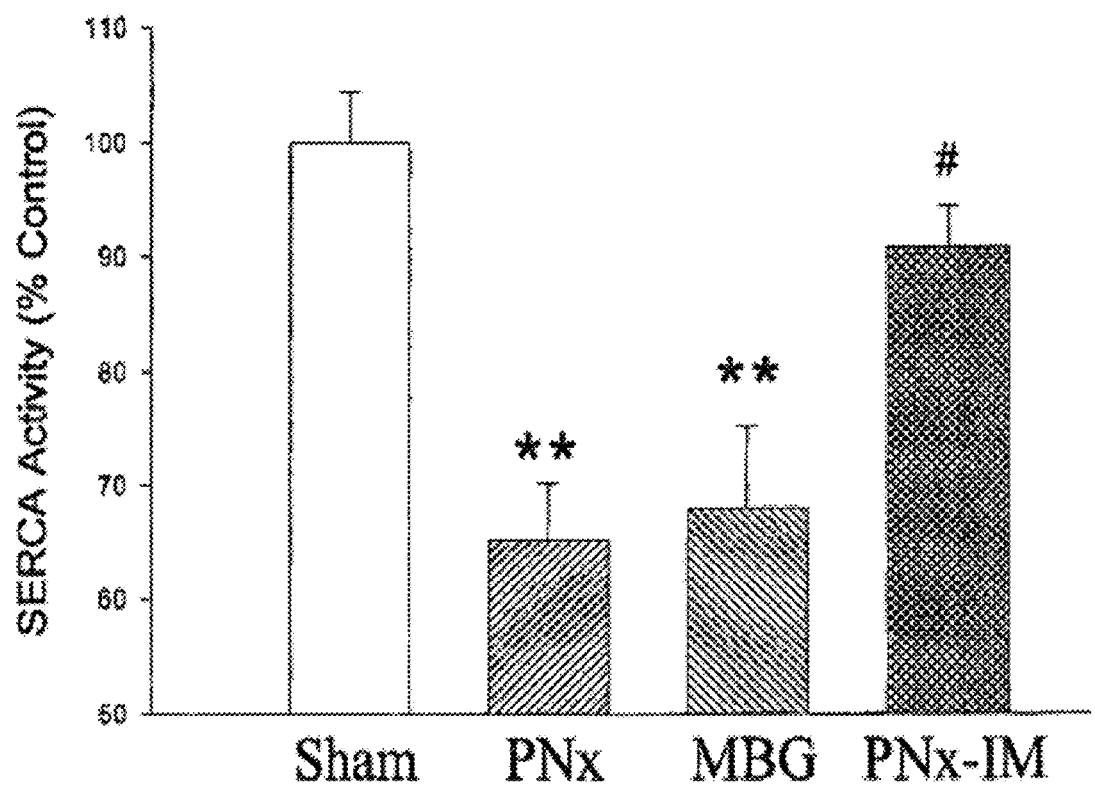
FIG. 7(h) shows SERCA expression demonstrated with Western blot.

FIGS. 5(a) and (b) show the effect of MBG on procollagen expression.

FIGS. 6 (a), (b), (c) and (d) MBG produces hemodynamic changes consistent with diastolic dysfunction. (a) Maximal rate of pressure change (+dP/dt). (b) ratio of +dP/dt to minimal rate of pressure change (i.e., most negative rate of pressure change, −dP/dt). (c) left ventricular end diastolic pressure (LVEDP) and (d) time constant of isovolumic relaxation four weeks after sham operation (Sham, n=14), partial nephrectomy (PNx, n=15), MBG infusion (MBG, n=12), or immunization against MBG before partial nephrectomy (PNx-IM, n=14). *P<0.05 vs. Sham; **P<0.01 vs Sham; #P<0.05 vs. PNX; ##P<0.01 vs. PNx.

FIG. 7(a) to (h) MBG produces changes in cardiac morphology and protein expression consistent with experimental uremia. (a) Heart weight/body weight (HW/BW) ratio 4 weeks after sham operation (Sham, n=18), partial nephrectomy (PNx, n=20), MBG infusion (MBG, n=20), or immunization against MBG before partial nephrectomy (PNx-IM, n=18). (b) Extracellular signal-related kinase (ERK-1, p44) activation in the left ventricular cardiac homogenate 4 weeks after Sham (n=15), PNx (n=14), MBG (n=7), or PNx-IM (n=7). Gels were loaded with 50-μg left ventricle homogenate protein. Representative active and total ERK blots shown. (c) Src (Src $pY^{418}$) activation in the left ventricular cardiac homogenate 4 weeks after Sham (n=15), PNx (n=13), MBG (n=10), or PNx-IM (n=6). Gels were loaded with 75-m left ventricle homogenate protein. Representative active and total Src blots shown. (d) Skeletal muscle actin (skACT), (e) Na/K-ATPase a1, (f) Na/K-ATPase a2, and (g) SERCA2a expression 4 weeks after Sham (n=15), PNx (n=13), MBG (n=10), or PNx-IM (n=B). Gels for d through g were loaded with 20 μg left ventricle homogenate protein. (h) SERCA2a enzymatic activity in the left ventricular cardiac homongenate 4 weeks after Sham (n=8), PNx (n=6), MBG (n=8), or PNx-IM (n=8). Bar graphs for Western blot data summarize densitometry analysis of the blots. **P<0.01 vs. Sham, *P<0.05 vs Sham, #P<0.05 vs. PNx, ##P<0.01 vs PNx.

Figure 8A:
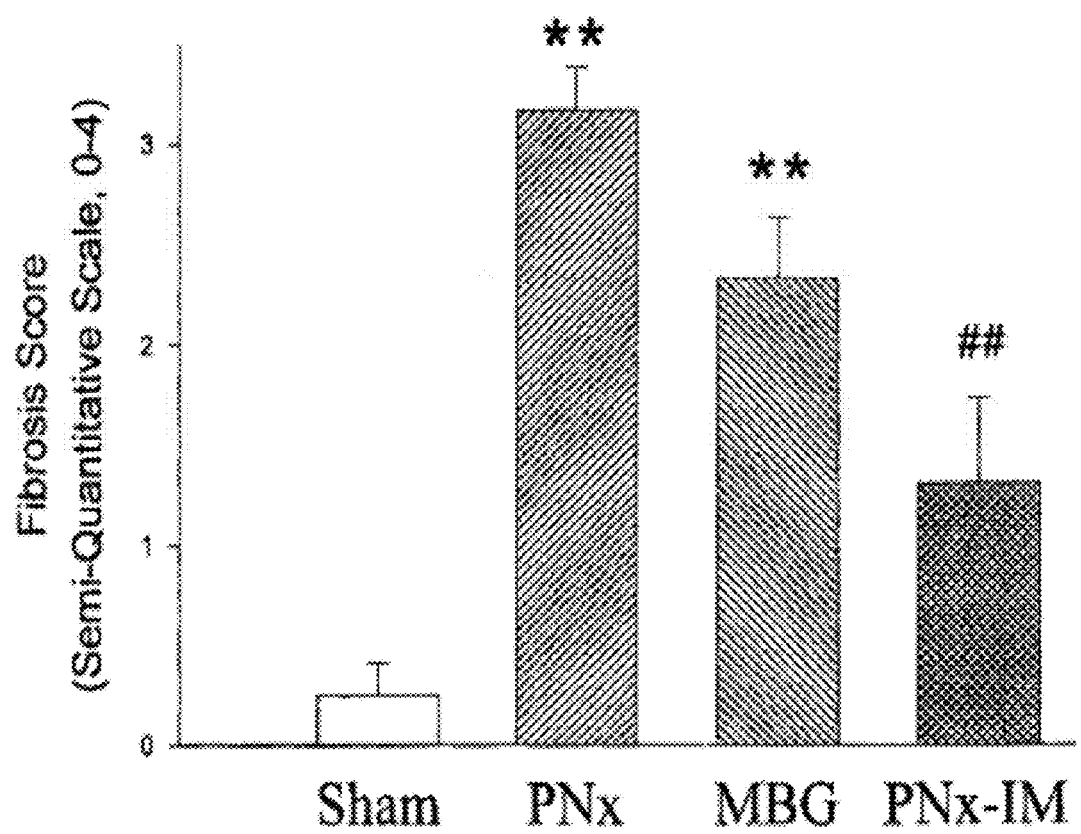
FIG. 8(a) shows Fibrosis-score data.
Figure 8B:
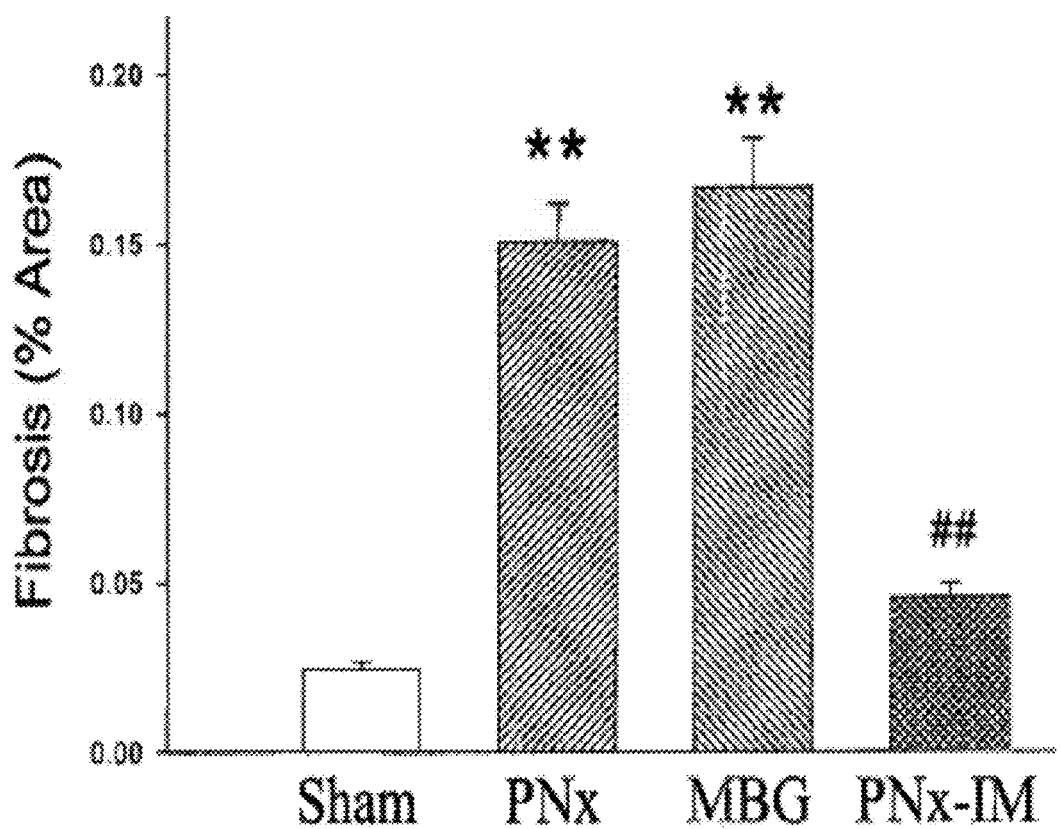
FIG. 8(b) shows Fibrosis data.
Figure 8C:
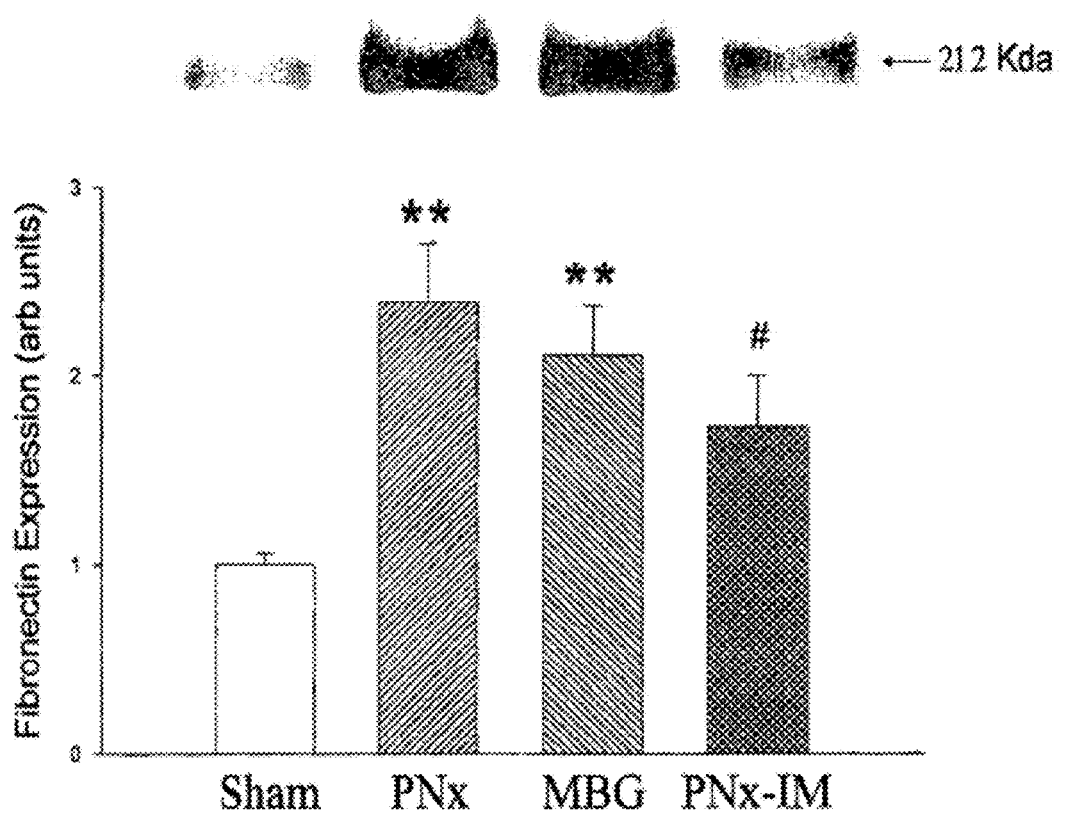
FIG. 8(c) shows Fibronectin Expression data.

FIGS. 8(a) and (b) show MBG induces cardiac fibrosis. (a) Representative Masson's trichrome sections of left ventricular cardiac tissue 4 weeks after sham operation (Sham), partial nephrectomy (PNx), MBG infusion (MBG), or immunization against MBG before partial nephrectomy (PNx-IM). (b) Semiquantitative grade and (c) quantitative morphometric fibrosis scoring for trichrome slides of left ventricular cardiac sections 4 weeks after Sham (n=8), PNx (n=10), MBG (n=10), or PNx-IM (n=10). (d) Fibronectin expression and quantified data from Sham (n=9), PNx (n=9), MBG (n=9), and PNx-IM (n=9). Gels were loaded with 50 μg of left ventricle homogenate protein. *P<0.05, **P<0.01 vs Sham, #P<0.05, ##P<0.01 vs. PNx.

Cardiotonic steroids (CTS) include plant-derived digitalis drugs such as digoxin and ouabain, and vertebrate-derived aglycones such as bualin and marinobufagen. Although CTS have been considered only as drugs since their discovery, recent studies have identified both ouabain and marinobufagenin as endogenous steroids whose production and secretion are regulated by multiple pathological or physiological stimuli including ACTH and angiotensin II. The effects of ouabain and marinobufagenin on blood pressure have now been well-documented. In addition, we and others have shown recently that low doses of these steroids not only induced hypertension in rats, but also caused significant cardiovascular remodeling independent of their effect on blood pressure. In addition, these steroids regulate cell growth and cellular production of extracellular matrix proteins including collagen.

It is well established that CTS are specific ligands and inhibitor of the Na/K-ATPase. Early studies have demonstrated that CTS regulates gene expression and cell growth. Recent work from our laboratories has made the connection between the Na/K-ATPase-mediated signal transduction and CTS-evoked changes in cellular function, showing that the Na/K-ATPase can transmit extracellular CTS signal via mechanisms independent of changes in intracellular Na+ and K+ concentrations. The signaling NA/K-ATPase resides in caveolae and forms a receptor complex with the tyrosine kinase Src. CTS such as ouabain act as agonists and provoke this receptor, resulting in tyrosine phosphorylation of the proteins that are either associated with or in close proximity to the signaling Na/K-ATPase/Src complex. Subsequently, this transactivates receptor tyrosine kinases such as EGFR and initiates protein kinase cascades. The identified pathways include the activation of PI3K, the Ras/Raf/ERKs and PLC/PKC isozymes. It also increases mitochondrial production of reactive oxygen species (ROS). Like other complex, activation of this complex by CTS induces the endocytosis of the activated complex, thus terminating the activated complex or targeting it to specific intracellular compartment. Unlike some of the RTKs, the signaling Na/K-ATPase can also function as a scaffold, capable of interacting with other membrane transporters and channels (FIG. 1). For instance, we have shown that the scaffolding and the kinase-regulatory capacities of the signaling Na/K-ATPase made it possible for the ouabain to induce $Ca^{2+}$ transients in cultured LLC-PK1 cells.

Immunohistochemistry studies of cardiac tissue obtained from rats with Sham surgery, experimental renal failure (PNx), MBG supplementation through mini-pumps (MBG), and rats immunized against MBG prior to PNx surgery. We noted the presence of protein (procollagen on left panel, a smooth muscle actin on right panel) (not shown). Similar pictures were obtained with vimentin or fibronectin. Western blot data confirms visual trends shown above (data not shown).

Based on these data, we next chose to examine whether MBG had direct effects on fribroblasts in a cell culture system. The following data illustrate our findings to date.

Procollagen expression as a function of MBG concentration. Top panel is western blot, bottom panel mean+/−SEM of 10 experiments.  $p<0.01$ vs Control Proline incorporation into collagen by cardiac fibroblasts is induced by MBG in a dose-dependent manner. Data shown as mean+/−SEM of 6 experiments  $p<0.01$ vs Control (horizontal bar at 1).

We next examined whether skin fibroblasts lines had similar response. This was done with dermal fibroblasts kindly provided by Dr. Bashar Kahaleh. Using these human cells grown in culture, we noted that dermal fibroblasts had an enormous response to MBG as shown below. The magnitude of this response is illustrated by comparison to maximal doses of TGFβ, the "classic" stimulus for fibrosis (see below). In addition, we observed that an immortalized fibroblast line responded similarly to MBG, ouabain and digoxin.

Response of dermal fibroblasts to MBG as compared with TGF beta. Note that increase in collagen expression in MBG is approximately 10 fold with 5 or 10 nM MBG. Comparable effect of ouabain, MBG and digoxin on fibroblast cell line expression of procollagen demonstrated with Western blot.

To sum these data, we observed that procollagen expression was markedly increased by cardiotonic steroids such as MBG. In other studies not shown here, we observed that the signaling through the Na/K-ATPase appeared to be essential for the profibrotic effect. Moreover, we observed that antagonism of signaling through this cascade by ROS scavenging, Src inhibition or prevention of EGFR transactivation prevented the induction of collagen synthesis.

Procollagen expression induced by MBG can be attenuated by Src inhibition (PP2), non-specific tyrosine kinase inhibition (Herbimycin) or prevention of EGFR transactivation (AG178). Top panel is representative Western blot, bottom panel is mean+/SEM of 6 experiments. ** $P<0.01$ vs Control. Collagen synthesis assessed by proline incorporation is increased by MBG. However both N-Acetyl Cysteine (NAC) and PP2 prevent this.

Next, we examined whether wound healing might be advantageously impacted by cardiotonic steroids. We grew a mouse fibroblast cell line, the SYF+Src line to confluence and make injuries by scraping with a pipette tip. We observed in this in vitro model of wound healing that 12 hour pretreatment with MBG markedly accelerated the closure of the experimental lesion (see below).

Representative images from fibroblasts at 3, 7 and 12 hours following injury. Quantification of wound closure from fibroblast cultures. Data represents N=6 separate pairs of experiments, each of which involves 3 determinations at each time point. Data shown as mean+/−SEM. **<0.01. We proposed to enhance skin fibroblast collagen production by topical or injected administration of cardiotonic steroids and prevent or reverse aging related loss of skin tone.

We also propose to develop a topical or systemic enhancement to wound closure.

Finally, by antagonism of this process, we propose to develop a topical or injected tool to reverse or prevent excessive dermal scar formation (e.g., keloids).

In another embodiment, we have observed recently that experimental renal failure in the rat is accompanied by increases in circulating concentrations of the cardiotonic steroid, marinobufagenin (MBG), and substantial cardiac fibrosis. We performed the following studies to examine whether MBG might directly stimulate cardiac fibroblast collagen production. In vivo studies were performed using the $\frac{5}{6}^{th}$ nephrectomy model of experimental renal failure (PNx), MBG infusion (MBG), PNx after immunization against MBG, and concomitant PNx and adrenalectomy. Physiological measurements with a Millar catheter and immunohistochemistry were performed. In vitro studies were then pursued with cultured isolated cardiac fibroblasts. We observed that PNx and MBG increased MBG levels, blood pressure, heart size, impaired diastolic function, and caused cardiac fibrosis. PNx after immunization against MBG and concomitant PNx and adrenalectomy had similar blood pressure as PNx but less cardiac hypertrophy, diastolic dysfunction, and cardiac fibrosis. MBG induced increases in procollagen-1 expression by cultured cardiac fibroblasts at 1 nM concentration. These increases in procollagen expression were accompanied by increases in collagen translation and increases in procollagen-1 mRNA without any demonstrable increase in procollagen-1 protein stability. The stimulation of fibroblasts with MBG could be prevented by administration of inhibitors of tyrosine phosphorylation, Src activation, epidermal growth factor receptor transactivation, and N-acetyl cysteine. Based on these findings, we propose that MBG directly induces increases in collagen expression by fibroblasts, and we suggest that this may be important in the cardiac fibrosis seen with experimental renal failure.

We have demonstrated previously that the cardiotonic steroid marinobufagenin (MBG), signaling through the Na/K-ATPase, is directly responsible for many features of experimental uremic cardiomyopathy induced by partial nephrectomy (PNx) in the rat. Specifically, we noted that both rats subject to PNx, as well as rats given MBG supplementation by minipump, developed considerable cardiac hypertrophy and fibrosis by 4 weeks, whereas rats immunized against MBG and subsequently subjected to PNx had attenuation of these changes. From these data, we formulated the hypothesis that MBG might directly induce cardiac fibroblasts to produce collagen, thus producing much of the cardiac fibrosis seen with experimental renal failure. To test this hypothesis and to determine the molecular basis by which this occurred, the following studies were performed.

EXAMPLES

Methods
Animals
Male, Sprague-Dawley rats were used for all of the studies. All of the animal experimentation described in the article was conducted in accordance with the National Institutes of Health Guide for the Care and use of Laboratory Animals using protocols approved by the Medical University of Ohio Institutional Animal Use and Care Committee.

Experimental Groups
Briefly, Sprague-Dawley rats weighing.apprxeq.250 g at the time of surgery were subjected to either sham surgery with no MBG infusion (Sham), sham surgery with placement of a minipump infusing MBG at 10 μg/kg per day (MBG), PNx, and PNx after immunization against MBG (PNx-IM). MBG of extremely high purity (>99%) was isolated from the venom of *Bufa marinas* by Kennedy et al. In addition to these maneuvers, a group of PNx animals was subjected to adrenalectomy as well (PNx-ADx).

The heart weight normalized to body weight, left ventricular hemodynamics (e.g. .tau. value, slope of regression line fit to end diastolic pressure versus end diastolic volume generated by inferior vena cava occlusions, all determined with a Millar catheter), plasma [MBG] (determined after extraction on a C-18 column using DELPHIA as described previously), aldosterone (determined with ELISA kit 10004377, Cayman Chemical) and cardiac immunohistochemistry (vida infra) were assessed 4 weeks after surgery.

Isolated Cardiac Fibroblasts
Preparation of adult rat cardiac fibroblasts was performed as described previously by Brilla et al. with modifications.

Western Blot Analysis
Western blot analysis was performed on protein isolated from tissue homogenates, cell culture whole cell lysates, or nuclear extracts as described previously.

Collagen Synthesis
Collagen synthesis rates were determined by the method of Nishida et al. with modification.

Quantitative Measurement of Collagen-1 mRNA
Standardized RT-PCR was used to measure gene expression, with GAPDH transcript used as the housekeeping gene, as reported previously.

Results
Effect of Experimental Renal Failure and MBG on Blood Pressure, Cardiac Hyemodynamics, and Fibrosis
In the current in vivo studies we observed that MBG levels were increased in PNx- and MBG-treated rats compared with sham-operated controls. We also saw that both PNx and MBG rats had higher systolic blood pressure than controls and that PNx-IM rats had statistically similar systolic blood pressure values as seen with PNx. Using the Millar pressure/volume sensor catheter rather than echocardiography in our previous report, we observed that PNx induced decreases in end systolic volume and end diastolic volume, as well as increased ejection fraction compared with sham-operated controls. The end systolic volume and end diastolic volume were greater, and the ejection factor values were lower in PNX-IM as compared with PNx. Active relaxation assessed was found to be impaired by both PNx and MBG compared with sham-operated controls, with PNX-IM showing lower values than PNx. Using pressure volume loops generated during vena cava occlusions, we noted that the end diastolic pressure volume relationship (an inverse measurement of passive compliance) was increased in PNx- and MBG-treated animals compared with controls, whereas PNx rats ha a lower end diastolic pressure volume relationship than PNx. Both PNx and MBG treatment increased the heart weight/body weight ratio compared with sham-operated controls, whereas PNx-IM animals had lower values than PNx. Examining the ventricular myocyte cross-sectional area determined on trichrome images, we noted that PNx and MBG infusion both induced marked increases, whereas the myocyte cross-sectional area in PNx-IM was considerably smaller than that seen with PNx alone.

Effects of PNx, MBG, and PNx-IM on Hemodynamics and Plasma MBG

TABLE

| Measurement | Sham | PNx | MBG | PNx-IM | PNx-ADx |
|---|---|---|---|---|---|
| Plasma MBG, pmol/L | 227 ± 27 | 527 ± 36 | 484 ± 47 | 396 ± 65 | 325 ± 65 |
| Plasma aldosterone, pg/mL | 184 ± 32 | 2012 ± 320 | 205 ± 35§ | 2492 ± 493 | 228 ± 65 |
| Tall cuff measurements | | | | | |
| Heart rate, bpm | 367 ± 7 | 388 ± 9 | 367 ± 9 | 380 ± 6 | 365 ± 7 |
| Systolic blood pressure, mm Hg | 102 ± 2 | 197 ± 6 | 136 ± 4 | 180 ± 9 | 193 ± 6 |
| Ventricular hemodynamics | | | | | |
| End systolic volume, μL | 70 ± 4 | 35 ± 4 | 60 ± 6 | 68 ± 9 | 56 ± 5 |
| End diastolic volume, μL | 190 ± 11 | 151 ± 10 | 162 ± 14 | 188 ± 15 | 185 ± 14 |
| Ejection fraction, % | 73 ± 1 | 79 ± 2 | 68 ± 2* | 71 ± 1 | 72 ± 2§ |

TABLE-continued

| Measurement | Sham | PNx | MBG | PNx-IM | PNx-ADx |
|---|---|---|---|---|---|
| τ, ms | 10.0 ± 0.3 | 14.5 ± 0.9 | 11.3 ± 0.3* | 31 ± 3* | 38 ± 4 |
| EDPVRX1000, mm Hg/μL | 24 ± 2 | 52 ± 4 | 41 ± 6 | 31 ± 3* | 38 ± 4 |
| Heart weight/body weight ratio, g/kg | 2.5 ± 0.1 | 3.6 ± 0.2 | 2.8 ± 0.1* | 2.9 ± 0.1 | 3.3 ± 0.1 |

Analyses were performed 4 weeks after sham operation (Sham, n = 20), partial nephrectomy (PNx, n = 20), MBG Infusion (MBG, n = 20), or immunization against MBG prior to partial nephrectomy (PNx-IM, n = 20).
Results repoted as mean ± SEM.

Analyzing the immunohistochemistry results, heart tissues from rats subjected to MBG and PNx showed marked increases in collagen-1 and a smooth muscle acting staining. Immunization against MBG attenuated these increases. Western blot analysis confirmed that PNx and MBG had 2 to 2.5 times the expression of procollagin-1 and a smooth muscle actin seen with sham-operated controls, whereas PNx-IM expression of both procollagen-1 and a smooth muscle actin was substantially less than that seen with PNx.

To determine the molecular mechanism underlying this fibrosis, we examined the expression of several proteins important in fibroplast activation. Specifically, we examined tissue levels of transforming growth factor (TGF)-β, Smad 2/3, and Smad 4, as well as pSmad 2/3. We did not detect significant differences among the experimental groups in the cardiac expression of these proteins.

A separate group of animals (N=11) was also subjected to PNx-ADx with physiological replacement of glucocorticoids and aldosterone. These animals developed a similar degree of hypertension compared with PNx but were noted to have much lower plasma MBG and aldosterone levels, as well as substantially lower heart/weight body weight ratio compared with PNx alone (Table). Moreover, these animals subjected to PNx-ADx had almost no evidence for cardiac fibrosis based on trichrome staining or immunohistochemistry staining for collagen-1 or a smooth muscle action.

Effect of Cardiotonic Steroids on Fibroblast Collagen Expression

To further examine the molecular basis of this cardiac fibrosis, isolated cardiac fibroblasts were subjected to increase doses of MBG ($10^{-10}$, $10^{-9}$, and $10^{-8}$ M). After 24 hours of exposure to $10^{-9}$ and $10^{-8}$ M MBG, procollagen content determined by Western blot was increased about 2 fold (both P<0.01; FIG. 5a). This phenomenon was not specific for MGB; other cardiotonic steroids also induced similar increases in procollagen content. Of interest, the threshold for effect for MBG seemed to be between $10^{-10}$ and $10^{-9}$M, whereas for ouabain, which circulates at similar concentrations in uremic rats, the threshold was .approx eq.10 times higher (i.e., between $10^{-9}$ and $10^{-8}$ M). For both MBG and ouabain, the threshold for inducing collagen expression was log units below the doses necessary for detectable effects on $^{86}$Rb uptake in these cells. In parallel studies examining radiolabeled proline incorporation into collagen, we observed that $10^{-9}$ and $10^{-8}$ M MBG induced significant increases in both proline incorporation into total protein, both matrix and supernatant. Using collagenase digestion, we observed that the vast majority of the proline incorporation was into collagen. Using standardized RT-PCR, we observed a doubling of mRNA for collagen-1 at 24 hours in response to 10 nM of MBG. However, we did not detect any increases in procollagen stability (determined by examining procollagen-1 expression after exposure to cycloheximide) in response to this concentration of MBG.

Effect of Inhibition of Na/K-ATPase Signaling on MBG-Stimulated Collagen Expression To examine whether cardiotronic steroids induced collagen synthesis by signaling through the Na/K-ATPase, we performed the following studies. First, we used pharmacological antagonism at several steps in the Na/K-ATPase cascade. Specifically, we used pharmacological antagonism of Src activation with PP2, nonspecific tyrosine kinase inhibition with herbimycin, inhibition of EGFR transactivation with AG1478, and nonspecific antioxidant administration with N-acetyle cysteine. Each of these maneuvers prevented MBG stimulation of collagen synthesis. To confirm these data, we also examined radiolabeled proline incorporation in response to MBG in the presence and absence of either PP2 or N-acetyl cysteine. As was the case for procollagen expression, both PP2 and N-acetyl cysteine prevented increases in proline incorporation into collagen in the primary fibroblast cultures. Next we performed studies in the SYF and SYF+ cells (details available in the online supplement). SYF+ cells responded to MBG and ouabain in a very similar way as the primary cardiac fibroblast cultures with respect to upregulation of procollagen expression, whereas the SYF cells had essentially no response to either MBG or ouabain.

Relationship Between TGF-β and MBG-Stimulated Collagen Production

To further examine the molecular mechanisms by which cardiotonic steroids induce collagen production in fibroblasts, we examined the effects of MBG on TGF-β expression, as well as the expression of Smad 2/3, Smad 4, and pSmad 2/3. As was the case for the in vivo experiments described earlier, we did not observe significant changes in TGF-β, Smad 2/3, Smad 4, or pSmad 2/3 expression in vitro. Next, we examined whether TGF-β induced collagen production and whether there was synergism between TGF-β and MBG. In the primary cultured cells, we saw similar effects of TGF-β (5 ng/mL) on procollagen expression as observed with cardiotonic steroids; however, we did not note any synergism between TGF-β (5 ng/mL) and MBG (10 nM). However, it is important to point out that we never completely serum starve the primary cultures, and because serum is always present, some TGF-β is always present.

To address this further, we also examined the effect of the TGF-β receptor antagonist, SB431542, on MBG stimulated collagen production. Interestingly, SB431542 at 100-μmol/L concentration did not educe procollagen expression below baseline on our Western blots but did decrease radiolabeled proline incorporation below that seen with control cells. the SB431542 completely blocked both TGF-β and MBG (10 nM) stimulation of collagen expression and radiolabeled proline incorporation.

Cardiac fibrosis is an important component of many cardiomyopathies, and it is a very characteristic component of uremic cardiomyopathy. Our group and others have observed that MBG and other cardiotonic steroids induce a signal transduction cascade through the plasmalemmal Na/K-ATPase residing in caveolae, which results in activation of Src, transactivation of the EGFR, generation of reactive oxygen species, and, ultimately, activation of p42/44 mitrogen-activated protein kinase. Interestingly, a number of clinical situations associated with cardiac fibrosis other than renal failure are associated with increased circulating concentrations of cardiotonic steroids (e.g., hypertension, primary hyperaldosteronism, and congestive heart failure). Although it is preliminary to discuss the possible relevance of our findings to cardiomyopathies other than renal failure, we should point out that Ferrandi et al. have observed that antagonism of endogenous cardiotonic steroids with PST 2238 ameliorates hypertension, as well as cardiac hypertrophy in Milan hypertensive rats.

In the current study, we confirmed that PNx and MBG treatment induce similar but not identical phenotypic changes in hemodynamics, and cardiac morphology. It is quite likely that some factors other than MBG contribute to the phenotypic changes seen in PNx. That said, both PNx-IM and PNx-ADx, which reduce circulating MBG, substantially attenuate the cardiac functional and morphological changes without significantly affecting blood pressure. We should point out that experiments in the PNx-ADx model were performed because we reasoned that as adrenal cells grown in culture seem to make MBG, it was likely that this procedure would lower the circulating levels of this hormone. However, whereas our data in the PNx-ADx animals support the concept that the adrenal gland is the major (but not the only) site of MBG production in vivo, it is also possible that other hormones made in the adrenal gland modulate MBG production elsewhere. Further work will be necessary to clarify exactly where MBG is produced under normal and pathological conditions.

With these findings implicating MBG in the pathogenesis of cardiac fibrosis, we were particularly interested in the molecular mechanisms underlying the fibrosis. Interestingly, evidence for increases in TGF-$\beta$ or signaling through the Smad proteins was not evident. We stress that these data do not exclude a role for TGF-$\beta$ in this process, because earlier increases in these proteins, translocation of the Smads, and/or a permissive role for signaling through this pathway (vida infra) could certainly be present.

Based on these in vivo data, we pursued studies in isolated cardiac fibroblasts. We observed that MBG in physiological concentrations directly stimulated the fibroblasts to produce more collagen. This increase in collagen production was also observed with other cardiotonic steroids, although the threshold concentration seemed to be .approxeq.1 log until owe for MBG than for ouabain. We emphasize that the concentration of both MBG and ouabain necessary to stimulate collagen expression was lower for both substances than that needed to appreciably inhibit Rb uptake. Further evidence for this phenomenon being dependent on signaling through the Na/K-ATPase was that this increase was prevented by reactive oxygen species scavenging, antagonism, or knockout of Src, as well as prevention of EGFR transactivation, maneuvers that we have demonstrated previously to block signal transduction through the Na/K-ATPase signalosome. We also observed that the increases in collagen production were associated with increases in proline incorporation, as well as increases in mRNA for collagen-1. No increase in procollagen-1 stability could be demonstrated in response to MBG.

Although increases in TGF-$\beta$ or the Smad proteins were also absent in the fibroblasts treated with MBG, it is important to note that the fibroblasts that we studied were never truly serum starved. The fibroblasts were exposed to .gtoreq.0.12 ng/mL of TGF-$\beta$ even when cultured in the serum-depleted (1% FBS) medium. This may, in part, explain why SB431542 was to effective in preventing MBG-stimulated collagen production. Working with a similar preparation, Lijnen and Petrov noted that long incubations (48 hours) and high concentrations of TGF-$\beta$ (15 ng/mL) were necessary to induce maximal (2 times) increases in collagen production. We should also note that TGF-$\beta$ blockade with SB431542 actually decreased proline incorporation below baseline, even in the setting of MBG synthesis, although this same pharmacological maneuver only reduced procollagen expression to baseline when measured with Western blot. We suspect that other mechanisms of regulation of collagen synthesis (e.g. procollagen stability) might come into play when the TGF-$\beta$ pathway is interrupted, although we did not explore this point further in the current studies. On balance, our data argue, albeit preliminarily, against a major role for TGF-$\beta$ or upregulation of Smad proteins in cardiotonic steroid-induced increases in fibroblast collagen production.

Our data shows that, in our experimental rodent model, MBG is implicated in the pathogenesis of the cardiac fibrosis, and the concentrations of MBG that develop in this setting, as well as other cardiotonic steroids, have in vitro effects that are consistent with this observation. One issue that immediately comes to mind is whether the clinical use of digitalis might have similar effects. To this question, we would suggest the following possibilities. First, it may be that the free concentrations of digoxin that occur in vivo are not sufficient to induce substantial cardiac fibrosis. Total digoxin levels are typically maintained <2 ng/mL in patients treated with digoxin, a concentration that corresponds with .apprxeq.2.5-nM concentration. However, only 70% to 80% of the plasma digoxin is free, and the fee concentration might fall below the threshold level of digoxin necessary to stimulate human cardiac (or other tissue) fibroblasts. Perhaps more relevant, we observed a fairly flat dose-response curve to MBG and ouabain with respect to stimulation of fibroblast collagen production once the threshold for an effect was reached. We suggest that in the setting of heart failure, a condition known to have associated increases in MBG and other cardiotonic steroids, the addition of digoxin at therapeutic doses might not have a detectable effect. Finally, we would point out that a systemic examination of whether digoxin induces or influences cardiac fibrosis in humans has not been thoroughly investigated, although the clinical efficacy of this agent in treating congestive heart failure has been extensively examined. It is important to note that the rate at which humans develop cardiac fibrosis seems to be considerably slower than that seen with rodents, which might further obfuscate whether digoxin has profibrotic effects in clinical subjects.

In summary, we observed that concentrations of MBG similar to that which develop in experimental renal failure produced increased synthesis of collagen in primary cardiac fibroblasts grown in culture in a manner dependent on signaling through an Na/K-ATPase-Src-EGFR-reactive oxygen species signaling cascase. Should these data be confirmed in humans, this insight may provide useful therapeutic targets in clinical uremic cardiomyopathy.

CONCLUSION

Cardiac fibrosis is an important component of cardiac diseases seen in a variety of disease states. Our data in the experimental renal failure model suggest that cardiotonic steroids, such as MBG, may contribute in a very substantial role in the cardiac fibrosis seen in this setting. Because Increases in MBG are likely to accompany a variety of volume expansion states, the implications of our observations may extend to other situations complicated by cardiac fibrosis.

Other data includes a representative pressure-volume loops obtained during vena cava occlusion from rats subjected to sham surgery (Sham), PNx, MBG infusion (MBG), and PNx after immunization against an MBG-albumin conjugate (PNx-IM). Regression lines fit to the end systolic pressure volume relationship (ESPVR, dotted line) and the end diastolic pressure volume relationship (EDPVR, solid line). B, ventricular cross-sectional areas determined from trichrome stains of tissue obtained from Sham, PNx, MBG, and PNx-IM animals (each group: N=8 animals, .apprxeq.100 measurements averaged to determine mean for each animal; data shown as the group mean.+-.SEM using N-8). Representative immunohistochemistry images of cardiac tissues stained for (c) collagen-1 and (d) a smooth muscle actin (aSMA). Counterstain for both c and d was hematoxlyn. Western blot and corresponding densitometric analysis for (e) procollagen-1 and (f) aSMA. Note that both collagen-1 and aSMA staining are much more intense in the PNx and MBG groups compared with Sham, whereas the PNx-IM staining is similar to Sham. Similarly, procollagen and aSMA expression are substantially higher in PNx and MBG animals compared with Sham, whereas immunization against MBG (PNx-IM) attenuated the changes seen with PNx. Data for e and f are derived from N=6 experiments in each group and shown as mean.+-.SEM. Sham refers to hearts isolated from control animals, PNx refers to PNx, MBG refers to MBG supplemented, and PNx-IM refers to animals immunized against MGB before PNx surgery. *P<0.05, **P<0.01 vs Sham, #P<0.01 vs PNx.

Representative Western blot for and quantitative densitometric data are for (a) TGF-.beta.1, (b) Smad 213, (c) Smad 4, and (d) pSmad 2/3. Data derived from N=6 experiments in each group and shown as mean.+-.SEM. Note similar expression of these proteins in all of the 4 experimental groups.

Representative Western blot for procollagen and quantitative densitometric data obtained in response to different doses of (a) MBG (all N=10), (b) MBG 10 nM contrasted with different doses of ouabain (0.1 to 100 nM) and digoxin (10 nM; all N=8). c, ouabain sensitive Rb uptake as a function of MBG and ouabain concentration (N=4 at each concentration for both MBG and ouabain; data expressed as fraction of control). d, relative proline incorporation in the supernatant and matrix, both will and without collagenase digestion (total). Each group (controls and different doses of MBG) contains N=7 replicants. The difference between the total and after collagenase digestion is reported as collagen. The matrix is the sample that was obtained after removing supernatant and scraping the culture dish. e, mRNA for collagen 1 in MBG-treated (10 nM; N=8) or control (N=8) fibroblasts. f, procollagen stability after cycloheximide treatment. Time 0 is 1 hour after incubation with cycloheximide (20 µg/mL). Densitometric data displayed on log scale. Least-square regression line fit to control (CTL) and MBG data. Bars on quantitative graphs represent the mean.+-.SEM. *P<0.05 and **P<0.01 vs control.

The effects of PP2 (1 µmol/L), herbimycin (1 µmol/L), AG1478 (250 nM), and N-acetyl cysteine (2.5 mmol/L) on MBG (10 nM) stimulation of procollagen expression also were found. The PP2, herbimycin AG1478, and N-acetyl cysteine were administered from 2 hours before the addition of MBG and continued throughout the 24 hours of MBG incubation (total of 26 hours). Each bar represents the mean.+-.SEM of n=8 experiments. b, effects of PP2 (1 µmol/L) and N-acetyle cysteine (2.5 mmol/L) on MBG (10 nM)-stimulated proline incorporation into collagen. Again, the PP2 an N-acetyl cysteine were added 2 hours before exposure to MBG. Each bar represents the mean.+-.SEM of N=5 experiments. c, effects of MBG 10 nM on procollagen content in SYF and SYF+ cells. Representative Western blots are shown above quantitative data. SYF blots loaded with 15 µg of protein and SYF+blots loaded with 10 µg of protein. Each bar represents the mean.+-SEM of N-6 determinations In each group. **P<01.10 vs. control.

The effect of 24 hours of MBG (1 and 10 nM) on TGF-β, Smad 2/3, Smad 4, and pSmad 2/3 expression determined by Western blot. b and c, effects of 24 hours of MBG (10 nM), TGFβ(5 ng/mL), and the TGF-β receptor antagonist SB431542 (100 (1 µmol/L) on procollagen-1 expression (Western blot) and radiolabeled proline incorporation, respectively also were carried out. SB431542 was added 2 hours before exposure to either TGFβ or MBG (total of 26-hour exposure). Each bar represents the mean.+-.SEM of 6 to 8 determinations. *P<0.05, **P<0.01 vs. control.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

What is claimed is:

1. A method of treating aging related loss of skin tone comprising administering by injection or topical formulation a composition comprising a pharmacologically effective amount of at least one cardiac glycoside that binds to the Na/K-ATPase in a pharmaceutically or cosmetically acceptable vehicle, the effective amount ranging from about 0.1 nM to about 10 nM, wherein the composition enhances skin fibroblast collagen production to treat aging related loss of skin tone;

wherein the cardiac glycoside inhibits the Na/K-ATPase at a concentration similar to that of marinobufagenin (MBG).

2. The method of claim 1, wherein the cardiac glycoside is a cardenolide or a bufadienolide, wherein said concentration is log units above 0.1 nM.

3. The method of claim 1, wherein the cardiac glycoside is derived from either plants or animals, is semi-synthesized, or is synthesized.

4. The method of claim 1, wherein the cardiac glycoside is derived from plants.

5. The method of claim 1, wherein the composition is in a dosage form selected from the group consisting of suspension tablets, powders, sachets, cachets, elixirs, suspensions, emulsions, solutions, syrups, aerosols, ointments, creams, lotions, solutions, gels, and pastes.

6. The method of claim 1, wherein the cardiac glycoside functions as a stimulator of the Na/K-ATPase signalosome.

7. The method of claim 1, wherein the composition induces interaction of the Na/K-ATPase with lipids, protein kinases, phosphatases, ion channels, transporters, and other soluble membrane proteins to form various Na/K-ATPase signalosome complexes.

* * * * *